(12) United States Patent
Ng et al.

(10) Patent No.: US 8,522,784 B2
(45) Date of Patent: *Sep. 3, 2013

(54) MASK SYSTEM

(71) Applicant: ResMed Limited, Bella Vista (AU)

(72) Inventors: Eva Ng, Erskineville (AU); David James Lockwood, Seaford (AU); Jamie Graeme Wehbeh, Mosman (AU); Zoran Valcic, Chatswood (AU); Errol Savio Alex D'Souza, Hornsby Heights (AU); Matthew Eves, Manly Vale (AU); Mahsita Sari, Kensington (AU)

(73) Assignee: ResMed Limited, Bella Vista (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/747,772

(22) Filed: Jan. 23, 2013

(65) Prior Publication Data

US 2013/0133658 A1  May 30, 2013

Related U.S. Application Data

(63) Continuation of application No. 12/736,024, filed as application No. PCT/AU2009/000241 on Feb. 27, 2009.

(60) Provisional application No. 61/136,617, filed on Sep. 19, 2008, provisional application No. 61/064,406, filed on Mar. 4, 2008, provisional application No. 61/071,893, filed on May 23, 2008.

(51) Int. Cl.
*A62B 18/02* (2006.01)
*A62B 18/08* (2006.01)

(52) U.S. Cl.
USPC ............ 128/206.28; 128/205.25; 128/206.24; 128/206.21

(58) Field of Classification Search
USPC ............. 128/205.25, 206.21, 206.24, 206.28, 128/207.11
See application file for complete search history.

(56) References Cited

U.S. PATENT DOCUMENTS

| | | | |
|---|---|---|---|
| 364,394 | A | 6/1887 | Bright |
| 428,592 | A | 5/1890 | Chapman |

(Continued)

FOREIGN PATENT DOCUMENTS

| | | |
|---|---|---|
| AU | 91/77110 | 11/1991 |
| AU | 94/64816 | 12/1994 |

(Continued)

OTHER PUBLICATIONS

Notification of the First Office Action and English Translation, for corresponding Chinese Application No. 200980116004.3, issued Dec. 24, 2012, 12 pages.

(Continued)

Primary Examiner — Kristen Matter
(74) Attorney, Agent, or Firm — Nixon & Vanderhye, PLC

(57) ABSTRACT

A full face mask system for treatment of respiratory disorder with Continuous Positive Airway Pressure equipment suitable to generate a supply of gas at positive pressure to be delivered to a patient's airways, the mask system comprising a frame module; a cushion module provided to the frame module and adapted to form a seal with the patient's face; an elbow module provided to the frame module and adapted to be connected to an air delivery tube to deliver breathable gas to the patient; and headgear removably attachable to the frame module.

30 Claims, 13 Drawing Sheets

(56) References Cited

U.S. PATENT DOCUMENTS

| | | | |
|---|---|---|---|
| 443,191 | A | 12/1890 | Illing |
| 781,516 | A | 1/1905 | Guthrie, Jr. |
| 812,706 | A | 2/1906 | Warbasse |
| 1,081,745 | A | 12/1913 | Johnston et al. |
| 1,125,542 | A | 1/1915 | Humphries |
| 1,176,886 | A | 3/1916 | Ermold |
| 1,192,186 | A | 7/1916 | Greene |
| 1,206,045 | A | 11/1916 | Smith |
| 1,229,050 | A | 6/1917 | Donald |
| 1,282,527 | A | 10/1918 | Bidonde |
| 1,362,766 | A | 12/1920 | McGargill |
| 1,445,010 | A | 2/1923 | Feinberg |
| 1,502,450 | A | 7/1924 | Wood |
| 1,610,793 | A | 12/1926 | Kaufman |
| 1,632,449 | A | 6/1927 | McKesson |
| 1,653,572 | A | 12/1927 | Jackson |
| 1,710,160 | A | 4/1929 | Gibbs |
| 1,837,591 | A | 12/1931 | Shindel |
| 1,873,160 | A | 8/1932 | Sturtevant |
| 1,926,027 | A | 9/1933 | Biggs |
| 2,011,733 | A | 8/1935 | Shindel |
| 2,104,016 | A | 1/1938 | Biggs |
| 2,123,353 | A | 7/1938 | Catt |
| 2,127,136 | A * | 8/1938 | Pobirs ...................... 128/207.12 |
| 2,130,555 | A | 9/1938 | Malcom |
| 2,133,699 | A | 10/1938 | Heidbrink |
| 2,149,067 | A | 2/1939 | Otero |
| 2,166,164 | A | 7/1939 | Lehmberg |
| 2,245,658 | A | 6/1941 | Erickson |
| 2,245,969 | A | 6/1941 | Francisco et al. |
| 2,248,477 | A | 7/1941 | Lombard |
| 2,254,854 | A | 9/1941 | O'Connell |
| 2,317,608 | A | 4/1943 | Heidbrink |
| 2,353,643 | A | 7/1944 | Bulbulian |
| 2,371,965 | A | 3/1945 | Lehmberg |
| 2,376,871 | A | 5/1945 | Fink |
| 2,382,364 | A | 8/1945 | Yant |
| 2,415,846 | A | 2/1947 | Randall |
| 2,428,451 | A | 10/1947 | Emerson |
| 2,433,565 | A | 12/1947 | Korman |
| 2,438,058 | A | 3/1948 | Kincheloe |
| 2,473,518 | A | 6/1949 | Garrard et al. |
| D156,060 | S | 11/1949 | Wade |
| D161,337 | S | 12/1950 | Hill |
| 2,540,567 | A | 2/1951 | Bennett |
| 2,578,621 | A | 12/1951 | Yant |
| 2,590,006 | A | 3/1952 | Gordon |
| 2,625,155 | A | 1/1953 | Engelder |
| 2,641,253 | A | 6/1953 | Engelder |
| 2,693,178 | A | 11/1954 | Gilroy |
| 2,706,983 | A | 4/1955 | Matheson et al. |
| 2,749,910 | A | 6/1956 | Faulconer, Jr. |
| RE24,193 | E | 8/1956 | Emerson |
| 2,820,651 | A | 1/1958 | Phillips |
| 2,837,090 | A | 6/1958 | Bloom et al. |
| 2,868,196 | A | 1/1959 | Stampe |
| 2,875,757 | A | 3/1959 | Galleher, Jr. |
| 2,875,759 | A | 3/1959 | Galleher, Jr. |
| 2,881,444 | A | 4/1959 | Fresh et al. |
| 2,882,895 | A | 4/1959 | Galeazzi |
| 2,902,033 | A | 9/1959 | Galleher, Jr. |
| 2,917,045 | A | 12/1959 | Schildknecht et al. |
| 2,931,356 | A | 4/1960 | Schwarz |
| D188,084 | S | 5/1960 | Garelick |
| 2,939,458 | A | 6/1960 | Lundquist |
| 3,013,556 | A | 12/1961 | Galleher, Jr. |
| 3,042,035 | A | 7/1962 | Coanda |
| 3,117,574 | A | 1/1964 | Replogle |
| 3,182,659 | A | 5/1965 | Blount |
| 3,189,027 | A | 6/1965 | Bartlett, Jr. |
| 3,193,624 | A | 7/1965 | Webb et al. |
| 3,238,943 | A | 3/1966 | Holley |
| 3,288,138 | A | 11/1966 | Sachs |
| 3,315,672 | A | 4/1967 | Cunningham et al. |
| 3,315,674 | A | 4/1967 | Bloom et al. |
| 3,330,273 | A | 7/1967 | Bennett |
| 3,330,274 | A | 7/1967 | Bennett |
| 3,362,420 | A | 1/1968 | Blackburn et al. |
| 3,363,833 | A | 1/1968 | Laerdal |
| 3,545,436 | A | 12/1970 | Holloway |
| 3,556,122 | A | 1/1971 | Laerdal |
| 3,580,051 | A | 5/1971 | Blevins |
| 3,670,726 | A | 6/1972 | Mahon et al. |
| 3,682,171 | A | 8/1972 | Dali et al. |
| 3,700,000 | A | 10/1972 | Hesse et al. |
| 3,720,235 | A | 3/1973 | Schrock |
| 3,725,953 | A | 4/1973 | Johnson et al. |
| 3,739,774 | A | 6/1973 | Gregory |
| 3,750,333 | A | 8/1973 | Vance |
| 3,752,157 | A | 8/1973 | Malmin |
| 3,754,552 | A | 8/1973 | King |
| 3,796,216 | A | 3/1974 | Schwarz |
| 3,799,164 | A | 3/1974 | Rollins |
| D231,803 | S | 6/1974 | Huddy |
| 3,830,230 | A | 8/1974 | Chester |
| 3,861,385 | A | 1/1975 | Carden |
| 3,902,486 | A | 9/1975 | Guichard |
| 3,905,361 | A | 9/1975 | Hewson et al. |
| 3,910,261 | A | 10/1975 | Ragsdale et al. |
| 3,938,614 | A | 2/1976 | Ahs |
| 3,972,321 | A | 8/1976 | Proctor |
| 3,978,854 | A | 9/1976 | Mills, Jr. |
| 4,006,744 | A | 2/1977 | Steer |
| 4,062,357 | A | 12/1977 | Laerdal |
| 4,069,516 | A | 1/1978 | Watkins, Jr. |
| 4,077,404 | A | 3/1978 | Elam |
| D248,497 | S | 7/1978 | Slosek |
| D250,131 | S | 10/1978 | Lewis et al. |
| 4,120,302 | A | 10/1978 | Ziegler |
| 4,142,527 | A | 3/1979 | Garcia |
| 4,153,051 | A | 5/1979 | Shippert |
| 4,156,426 | A | 5/1979 | Gold |
| 4,167,185 | A | 9/1979 | Lewis |
| 4,201,205 | A | 5/1980 | Bartholomew |
| 4,226,234 | A | 10/1980 | Gunderson |
| 4,231,363 | A | 11/1980 | Grimes |
| 4,233,972 | A | 11/1980 | Hauff et al. |
| 4,239,038 | A | 12/1980 | Holmes |
| 4,245,632 | A | 1/1981 | Houston |
| 4,248,218 | A | 2/1981 | Fischer |
| 4,263,908 | A | 4/1981 | Mizerak |
| 4,264,743 | A | 4/1981 | Maruyama et al. |
| 4,265,239 | A | 5/1981 | Fischer, Jr. et al. |
| 4,266,540 | A | 5/1981 | Panzik et al. |
| 4,267,845 | A | 5/1981 | Robertson, Jr. et al. |
| 4,273,124 | A | 6/1981 | Zimmerman |
| D262,322 | S | 12/1981 | Mizerak |
| 4,304,229 | A | 12/1981 | Curtin |
| 4,312,359 | A | 1/1982 | Olson |
| 4,328,797 | A | 5/1982 | Rollins et al. |
| 4,337,767 | A | 7/1982 | Yahata |
| 4,347,205 | A | 8/1982 | Stewart |
| 4,354,488 | A | 10/1982 | Bartos |
| 4,367,735 | A | 1/1983 | Dali |
| 4,367,816 | A | 1/1983 | Wilkes |
| 4,369,284 | A | 1/1983 | Chen |
| 4,402,316 | A | 9/1983 | Gadberry |
| 4,406,283 | A | 9/1983 | Bir |
| 4,412,537 | A | 11/1983 | Tiger |
| 4,414,973 | A | 11/1983 | Matheson et al. |
| 4,417,575 | A | 11/1983 | Hilton et al. |
| 4,422,456 | A | 12/1983 | Teip |
| 4,446,576 | A | 5/1984 | Hisataka |
| 4,449,526 | A | 5/1984 | Elam |
| 4,454,880 | A | 6/1984 | Muto et al. |
| 4,454,881 | A | 6/1984 | Huber et al. |
| 4,455,675 | A | 6/1984 | Bose et al. |
| 4,458,679 | A | 7/1984 | Ward |
| 4,467,799 | A | 8/1984 | Steinberg |
| 4,493,614 | A | 1/1985 | Chu et al. |
| 4,522,639 | A | 6/1985 | Ansite et al. |
| 4,548,200 | A | 10/1985 | Wapner |
| 4,549,542 | A | 10/1985 | Chein |
| 4,558,710 | A | 12/1985 | Eichler |

| | | |
|---|---|---|
| 4,572,323 A | 2/1986 | Randall |
| 4,579,113 A | 4/1986 | McCreadie et al. |
| 4,587,967 A | 5/1986 | Chu et al. |
| 4,593,688 A | 6/1986 | Payton |
| 4,601,465 A | 7/1986 | Roy |
| D285,496 S | 9/1986 | Berman |
| 4,616,647 A | 10/1986 | McCreadie |
| 4,617,637 A | 10/1986 | Chu et al. |
| 4,622,964 A | 11/1986 | Flynn |
| 4,630,604 A | 12/1986 | Montesi |
| 4,641,645 A | 2/1987 | Tayebi |
| 4,641,647 A | 2/1987 | Behan |
| D289,238 S | 4/1987 | Arthur, Jr. |
| 4,655,213 A | 4/1987 | Rapoport et al. |
| 4,657,010 A | 4/1987 | Wright |
| 4,660,555 A | 4/1987 | Payton |
| 4,665,570 A | 5/1987 | Davis |
| 4,671,267 A | 6/1987 | Stout |
| 4,671,271 A | 6/1987 | Bishop et al. |
| 4,674,134 A | 6/1987 | Lundin |
| 4,676,241 A | 6/1987 | Webb et al. |
| 4,677,975 A | 7/1987 | Edgar et al. |
| 4,677,977 A | 7/1987 | Wilcox |
| 4,686,977 A | 8/1987 | Cosma |
| 4,699,139 A | 10/1987 | Marshall et al. |
| 4,706,664 A | 11/1987 | Snook et al. |
| 4,707,863 A | 11/1987 | McNeal |
| 4,711,636 A | 12/1987 | Bierman |
| 4,713,844 A | 12/1987 | Westgate |
| H397 H | 1/1988 | Stark |
| D293,613 S | 1/1988 | Wingler |
| 4,739,755 A | 4/1988 | White et al. |
| 4,753,233 A | 6/1988 | Grimes |
| 4,767,411 A | 8/1988 | Edmunds |
| 4,770,169 A | 9/1988 | Schmoegner et al. |
| 4,772,760 A | 9/1988 | Graham |
| 4,774,941 A | 10/1988 | Cook |
| 4,774,946 A | 10/1988 | Ackerman et al. |
| 4,782,832 A | 11/1988 | Trimble et al. |
| 4,790,829 A | 12/1988 | Bowden et al. |
| 4,799,477 A | 1/1989 | Lewis |
| 4,802,857 A | 2/1989 | Laughlin |
| 4,803,981 A | 2/1989 | Vickery |
| 4,807,617 A | 2/1989 | Nesti |
| 4,809,692 A | 3/1989 | Nowacki et al. |
| 4,811,730 A | 3/1989 | Milano |
| 4,819,629 A | 4/1989 | Jonson |
| 4,821,713 A | 4/1989 | Bauman |
| 4,827,924 A | 5/1989 | Japuntich |
| 4,830,138 A | 5/1989 | Palmaer et al. |
| 4,832,017 A | 5/1989 | Schnoor |
| 4,838,878 A | 6/1989 | Kalt et al. |
| 4,841,953 A | 6/1989 | Dodrill |
| 4,848,334 A | 7/1989 | Bellm |
| 4,848,366 A | 7/1989 | Aita et al. |
| 4,850,346 A | 7/1989 | Michel et al. |
| 4,856,118 A | 8/1989 | Sapiejewski |
| D304,384 S | 10/1989 | Derobert |
| 4,886,058 A | 12/1989 | Brostrom et al. |
| 4,899,740 A | 2/1990 | Napolitano |
| 4,905,683 A | 3/1990 | Cronjaeger |
| 4,907,584 A | 3/1990 | McGinnis |
| 4,910,806 A | 3/1990 | Baker et al. |
| 4,914,957 A | 4/1990 | Dougherty |
| 4,915,105 A | 4/1990 | Lee |
| 4,915,106 A | 4/1990 | Aulgur et al. |
| 4,919,128 A | 4/1990 | Kopala et al. |
| 4,919,654 A | 4/1990 | Kalt |
| 4,938,210 A | 7/1990 | Shene |
| 4,938,212 A | 7/1990 | Snook et al. |
| 4,941,476 A | 7/1990 | Fisher |
| 4,944,310 A | 7/1990 | Sullivan |
| 4,945,907 A | 8/1990 | Tayebi |
| 4,947,860 A | 8/1990 | Fisher |
| D310,431 S | 9/1990 | Bellm |
| 4,960,121 A | 10/1990 | Nelson et al. |
| 4,966,590 A | 10/1990 | Kalt |
| 4,969,880 A | 11/1990 | Zamierowski |
| 4,971,051 A | 11/1990 | Toffolon |
| D313,277 S | 12/1990 | Haining |
| 4,976,698 A | 12/1990 | Stokley |
| 4,986,269 A | 1/1991 | Hakkinen |
| 4,989,271 A | 2/1991 | Sapiejewski et al. |
| 4,989,596 A | 2/1991 | Macris et al. |
| 4,989,599 A | 2/1991 | Carter |
| 4,996,983 A | 3/1991 | AmRhein |
| 5,000,173 A | 3/1991 | Zalkin et al. |
| 5,003,631 A | 4/1991 | Richardson |
| 5,003,633 A | 4/1991 | Itoh |
| 5,005,568 A | 4/1991 | Loescher et al. |
| 5,005,571 A | 4/1991 | Dietz |
| 5,018,519 A | 5/1991 | Brown |
| 5,020,163 A | 6/1991 | Aileo et al. |
| 5,022,900 A | 6/1991 | Bar-Yona et al. |
| 5,023,955 A | 6/1991 | Murphy, II et al. |
| 5,025,805 A | 6/1991 | Nutter |
| 5,027,809 A | 7/1991 | Robinson |
| 5,038,772 A | 8/1991 | Kolbe et al. |
| 5,038,776 A | 8/1991 | Harrison et al. |
| 5,042,473 A | 8/1991 | Lewis |
| 5,042,478 A | 8/1991 | Kopala et al. |
| 5,046,200 A | 9/1991 | Feder |
| 5,046,491 A | 9/1991 | Derrick |
| 5,062,421 A | 11/1991 | Burns et al. |
| 5,063,922 A | 11/1991 | Hakkinen |
| 5,069,205 A | 12/1991 | Urso |
| 5,074,297 A | 12/1991 | Venegas |
| 5,080,092 A | 1/1992 | Tenna |
| D323,908 S | 2/1992 | Hollister et al. |
| 5,093,940 A | 3/1992 | Nishiyama |
| 5,109,839 A | 5/1992 | Blasdell et al. |
| 5,109,840 A | 5/1992 | Daleiden |
| 5,113,857 A | 5/1992 | Dickerman et al. |
| 5,117,818 A | 6/1992 | Palfy |
| 5,121,745 A | 6/1992 | Israel |
| 5,121,746 A | 6/1992 | Sikora |
| 5,123,677 A | 6/1992 | Kreczko et al. |
| 5,127,397 A | 7/1992 | Kohnke |
| 5,133,347 A | 7/1992 | Huennebeck |
| 5,137,017 A | 8/1992 | Salter |
| 5,138,722 A | 8/1992 | Urella et al. |
| 5,140,980 A | 8/1992 | Haughey et al. |
| 5,140,982 A | 8/1992 | Bauman |
| 5,146,914 A | 9/1992 | Sturrock |
| 5,159,938 A | 11/1992 | Laughlin |
| 5,178,138 A | 1/1993 | Walstrom et al. |
| 5,181,506 A | 1/1993 | Tardiff, Jr. et al. |
| D333,015 S | 2/1993 | Farmer et al. |
| 5,188,101 A | 2/1993 | Tumolo |
| D334,633 S | 4/1993 | Rudolph |
| 5,199,424 A | 4/1993 | Sullivan et al. |
| D335,322 S | 5/1993 | Jones |
| 5,207,665 A | 5/1993 | Davis et al. |
| 5,220,699 A | 6/1993 | Farris |
| 5,222,478 A | 6/1993 | Scarberry et al. |
| 5,231,983 A | 8/1993 | Matson et al. |
| 5,233,978 A | 8/1993 | Callaway |
| 5,243,709 A | 9/1993 | Sheehan et al. |
| 5,243,971 A | 9/1993 | Sullivan et al. |
| 5,245,995 A | 9/1993 | Sullivan et al. |
| 5,263,939 A | 11/1993 | Wortrich |
| 5,265,592 A | 11/1993 | Beaussant |
| 5,265,595 A | 11/1993 | Rudolph |
| 5,267,557 A | 12/1993 | Her-Mou |
| 5,269,296 A | 12/1993 | Landis |
| 5,271,391 A | 12/1993 | Graves |
| 5,279,289 A | 1/1994 | Kirk |
| 5,280,784 A | 1/1994 | Kohler |
| 5,291,880 A | 3/1994 | Almovist et al. |
| 5,299,448 A | 4/1994 | Maryyanek et al. |
| 5,299,579 A | 4/1994 | Gedeon et al. |
| 5,299,599 A | 4/1994 | Farmer et al. |
| 5,301,689 A | 4/1994 | Wennerholm |
| 5,304,146 A | 4/1994 | Johnson et al. |
| 5,311,862 A | 5/1994 | Blasdell et al. |
| 5,322,057 A | 6/1994 | Raabe et al. |
| 5,322,059 A | 6/1994 | Walther |
| 5,331,691 A | 7/1994 | Runckel |

| Patent | Date | Name |
|---|---|---|
| D349,586 S | 8/1994 | Handke |
| 5,334,646 A | 8/1994 | Chen |
| 5,335,656 A | 8/1994 | Bowe et al. |
| 5,343,878 A | 9/1994 | Scarberry et al. |
| 5,349,949 A | 9/1994 | Schegerin |
| 5,353,789 A | 10/1994 | Schlobohm |
| 5,355,878 A | 10/1994 | Griffiths et al. |
| 5,355,893 A | 10/1994 | Mick et al. |
| 5,357,945 A | 10/1994 | Messina |
| 5,357,951 A | 10/1994 | Ratner |
| 5,364,367 A | 11/1994 | Banks et al. |
| 5,372,130 A | 12/1994 | Stern et al. |
| 5,372,388 A | 12/1994 | Gargiulo |
| 5,372,389 A | 12/1994 | Tam et al. |
| 5,372,390 A | 12/1994 | Conway et al. |
| 5,372,391 A | 12/1994 | Bast et al. |
| 5,375,593 A | 12/1994 | Press |
| 5,385,141 A | 1/1995 | Granatiero |
| 5,388,571 A | 2/1995 | Roberts et al. |
| 5,390,373 A | 2/1995 | Flory |
| 5,391,248 A | 2/1995 | Brain |
| 5,394,568 A | 3/1995 | Brostrom et al. |
| 5,396,885 A | 3/1995 | Nelson |
| 5,398,676 A | 3/1995 | Press et al. |
| 5,400,776 A | 3/1995 | Bartholomew |
| 5,400,781 A | 3/1995 | Davenport |
| 5,404,871 A | 4/1995 | Goodman et al. |
| 5,419,317 A | 5/1995 | Blasdell et al. |
| 5,419,318 A | 5/1995 | Tayebi |
| 5,425,359 A | 6/1995 | Liou |
| 5,429,126 A | 7/1995 | Bracken |
| 5,429,683 A | 7/1995 | Le Mitouard |
| 5,431,158 A | 7/1995 | Tirotta |
| 5,437,267 A | 8/1995 | Weinstein et al. |
| 5,438,981 A | 8/1995 | Starr et al. |
| 5,441,046 A | 8/1995 | Starr et al. |
| D362,061 S | 9/1995 | McGinnis et al. |
| 5,462,528 A | 10/1995 | Roewer |
| 5,477,852 A | 12/1995 | Landis et al. |
| 5,479,920 A | 1/1996 | Piper et al. |
| 5,481,763 A | 1/1996 | Brostrom et al. |
| 5,485,837 A | 1/1996 | Solesbee et al. |
| 5,488,948 A | 2/1996 | Dubruille et al. |
| 5,492,116 A | 2/1996 | Scarberry et al. |
| 5,501,214 A | 3/1996 | Sabo |
| 5,503,147 A | 4/1996 | Bertheau |
| 5,509,404 A | 4/1996 | Lloyd et al. |
| 5,509,409 A | 4/1996 | Weatherholt |
| 5,511,541 A | 4/1996 | Dearstine |
| 5,513,634 A | 5/1996 | Jackson |
| 5,513,635 A | 5/1996 | Bedi |
| 5,517,986 A | 5/1996 | Starr et al. |
| 5,522,382 A | 6/1996 | Sullivan et al. |
| 5,526,806 A | 6/1996 | Sansoni |
| 5,533,506 A | 7/1996 | Wood |
| 5,538,000 A | 7/1996 | Rudolph |
| 5,538,001 A | 7/1996 | Bridges |
| 5,540,223 A | 7/1996 | Starr et al. |
| 5,542,128 A | 8/1996 | Lomas |
| 5,546,936 A | 8/1996 | Virag et al. |
| 5,558,090 A | 9/1996 | James |
| RE35,339 E | 10/1996 | Rapoport |
| 5,560,354 A | 10/1996 | Berthon-Jones et al. |
| 5,568,946 A | 10/1996 | Jackowski |
| 5,570,682 A | 11/1996 | Johnson |
| 5,570,684 A | 11/1996 | Behr |
| 5,570,689 A | 11/1996 | Starr et al. |
| 5,575,278 A | 11/1996 | Bonhomme et al. |
| D377,089 S | 12/1996 | Starr et al. |
| 5,592,937 A | 1/1997 | Freund |
| 5,592,938 A | 1/1997 | Scarberry et al. |
| 5,608,647 A | 3/1997 | Rubsamen et al. |
| 5,617,849 A | 4/1997 | Springett et al. |
| 5,623,923 A | 4/1997 | Bertheau et al. |
| 5,642,726 A | 7/1997 | Owens et al. |
| 5,642,730 A | 7/1997 | Baran |
| 5,645,054 A | 7/1997 | Cotner et al. |
| 5,647,355 A | 7/1997 | Starr et al. |
| 5,647,356 A | 7/1997 | Osendorf et al. |
| 5,647,357 A | 7/1997 | Barnett et al. |
| 5,649,532 A | 7/1997 | Griffiths |
| 5,649,533 A | 7/1997 | Oren |
| 5,653,228 A | 8/1997 | Byrd |
| 5,655,520 A | 8/1997 | Howe et al. |
| 5,655,527 A | 8/1997 | Scarberry et al. |
| 5,657,493 A | 8/1997 | Ferrero et al. |
| 5,657,752 A | 8/1997 | Landis et al. |
| 5,660,171 A | 8/1997 | Kimm et al. |
| 5,660,174 A | 8/1997 | Jacobelli |
| 5,662,101 A | 9/1997 | Ogden et al. |
| 5,666,946 A | 9/1997 | Langenback |
| 5,676,133 A | 10/1997 | Hickle et al. |
| D385,960 S | 11/1997 | Rudolph |
| 5,682,881 A | 11/1997 | Winthrop et al. |
| 5,685,296 A | 11/1997 | Zdrojkowski et al. |
| 5,687,715 A | 11/1997 | Landis et al. |
| D389,238 S | 1/1998 | Kirk, III et al. |
| 5,704,345 A | 1/1998 | Berthon-Jones |
| 5,707,342 A | 1/1998 | Tanaka |
| 5,709,204 A | 1/1998 | Lester |
| 5,715,814 A | 2/1998 | Ebers |
| 5,724,964 A | 3/1998 | Brunson et al. |
| 5,724,965 A | 3/1998 | Handke et al. |
| 5,735,272 A | 4/1998 | Dillon et al. |
| 5,740,799 A | 4/1998 | Nielson |
| 5,746,201 A | 5/1998 | Kidd |
| 5,752,509 A | 5/1998 | Lachmann et al. |
| 5,752,511 A | 5/1998 | Simmons et al. |
| 5,778,872 A | 7/1998 | Fukunaga et al. |
| 5,782,774 A | 7/1998 | Shmulewitz |
| 5,794,615 A | 8/1998 | Estes |
| 5,794,617 A | 8/1998 | Brunell et al. |
| 5,794,619 A | 8/1998 | Edelman et al. |
| D398,987 S | 9/1998 | Cotner et al. |
| 5,807,341 A | 9/1998 | Heim |
| 5,813,423 A | 9/1998 | Kirchgeorg |
| 5,832,918 A | 11/1998 | Pantino |
| D402,755 S | 12/1998 | Kwok |
| 5,842,469 A | 12/1998 | Rapp et al. |
| RE36,165 E | 3/1999 | Behr |
| 5,884,624 A | 3/1999 | Barnett et al. |
| 5,887,587 A | 3/1999 | Groenke |
| 5,896,857 A | 4/1999 | Hely et al. |
| 5,906,203 A | 5/1999 | Klockseth et al. |
| 5,909,732 A | 6/1999 | Diesel et al. |
| 5,918,598 A | 7/1999 | Belfer et al. |
| D412,745 S | 8/1999 | Scheu |
| 5,935,136 A | 8/1999 | Hulse et al. |
| 5,937,445 A | 8/1999 | Ravo et al. |
| 5,937,851 A | 8/1999 | Serowski et al. |
| 5,954,049 A | 9/1999 | Foley et al. |
| 5,964,485 A | 10/1999 | Hame et al. |
| 5,966,745 A | 10/1999 | Schwartz et al. |
| 5,970,975 A | 10/1999 | Estes et al. |
| 5,975,079 A | 11/1999 | Hellings et al. |
| 6,003,511 A | 12/1999 | Fukunaga et al. |
| 6,006,748 A | 12/1999 | Hollis |
| D419,658 S | 1/2000 | Matchett et al. |
| 6,016,804 A | 1/2000 | Gleason et al. |
| D421,298 S | 2/2000 | Kenyon et al. |
| 6,019,101 A | 2/2000 | Cotner et al. |
| 6,026,811 A | 2/2000 | Settle |
| 6,029,660 A | 2/2000 | Calluaud et al. |
| 6,029,665 A | 2/2000 | Berthon-Jones |
| 6,039,044 A | 3/2000 | Sullivan |
| D423,096 S | 4/2000 | Kwok |
| 6,044,844 A | 4/2000 | Kwok et al. |
| 6,082,360 A | 7/2000 | Rudolph et al. |
| 6,086,118 A | 7/2000 | McNaughton et al. |
| 6,091,973 A | 7/2000 | Colla et al. |
| D428,987 S | 8/2000 | Kwok |
| 6,095,996 A | 8/2000 | Steer et al. |
| 6,102,040 A | 8/2000 | Tayebi et al. |
| 6,109,263 A | 8/2000 | Feuchtgruber |
| 6,112,746 A | 9/2000 | Kwok et al. |
| 6,119,693 A | 9/2000 | Kwok et al. |
| 6,119,694 A | 9/2000 | Correa et al. |
| 6,123,071 A | 9/2000 | Berthon-Jones et al. |

| | | |
|---|---|---|
| 6,123,082 A | 9/2000 | Berthon-Jones |
| 6,139,787 A | 10/2000 | Harrison |
| 6,152,137 A | 11/2000 | Schwartz et al. |
| 6,155,253 A | 12/2000 | Gamberini |
| 6,192,886 B1 | 2/2001 | Rudolph |
| 6,193,914 B1 | 2/2001 | Harrison |
| D439,326 S | 3/2001 | Hecker et al. |
| 6,196,223 B1 | 3/2001 | Belfer et al. |
| 6,211,263 B1 | 4/2001 | Cinelli et al. |
| 6,213,125 B1 | 4/2001 | Reese et al. |
| 6,231,548 B1 | 5/2001 | Bassett |
| D443,355 S | 6/2001 | Gunaratnam et al. |
| 6,241,930 B1 | 6/2001 | Harrison |
| 6,257,237 B1 | 7/2001 | Suzuki |
| 6,257,626 B1 | 7/2001 | Campau |
| 6,258,066 B1 | 7/2001 | Urich |
| 6,279,573 B1 | 8/2001 | Johnson et al. |
| 6,295,366 B1 | 9/2001 | Haller et al. |
| 6,328,031 B1 | 12/2001 | Tischer et al. |
| 6,328,038 B1 | 12/2001 | Kessler et al. |
| 6,340,024 B1 | 1/2002 | Brookman et al. |
| 6,341,606 B1 | 1/2002 | Bordewick et al. |
| 6,345,618 B1 | 2/2002 | Hayek |
| 6,347,631 B1 | 2/2002 | Hansen et al. |
| 6,357,440 B1 | 3/2002 | Hansen et al. |
| 6,357,441 B1 | 3/2002 | Kwok et al. |
| 6,358,279 B1 | 3/2002 | Tahi et al. |
| 6,371,110 B1 | 4/2002 | Peterson et al. |
| 6,374,826 B1 | 4/2002 | Gunaratnam et al. |
| 6,388,640 B1 | 5/2002 | Chigira et al. |
| 6,397,847 B1 | 6/2002 | Scarberry et al. |
| 6,412,487 B1 | 7/2002 | Gunaratnam et al. |
| 6,412,488 B1 | 7/2002 | Barnett et al. |
| 6,412,593 B1 | 7/2002 | Jones |
| 6,418,928 B1 | 7/2002 | Bordewick et al. |
| 6,419,660 B1 | 7/2002 | Russo |
| 6,422,238 B1 | 7/2002 | Lithgow |
| 6,423,036 B1 | 7/2002 | Van Huzen |
| 6,425,395 B1 | 7/2002 | Brewer et al. |
| 6,427,694 B1 | 8/2002 | Hecker et al. |
| 6,431,172 B1 | 8/2002 | Bordewick |
| 6,434,796 B1 | 8/2002 | Speirs |
| 6,439,230 B1 | 8/2002 | Gunaratnam et al. |
| 6,439,234 B1 | 8/2002 | Curti et al. |
| 6,448,303 B1 | 9/2002 | Paul |
| 6,463,931 B1 | 10/2002 | Kwok et al. |
| 6,467,482 B1 | 10/2002 | Boussignac |
| 6,467,483 B1 | 10/2002 | Kopacko et al. |
| 6,470,887 B1 | 10/2002 | Martinez |
| 6,478,026 B1 | 11/2002 | Wood |
| 6,482,178 B1 | 11/2002 | Andrews et al. |
| 6,491,034 B1 | 12/2002 | Gunaratnam et al. |
| D468,823 S | 1/2003 | Smart |
| 6,513,526 B2 | 2/2003 | Kwok et al. |
| 6,520,182 B1 | 2/2003 | Gunaratnam |
| 6,530,373 B1 | 3/2003 | Patron et al. |
| 6,532,961 B1 | 3/2003 | Kwok et al. |
| 6,536,435 B1 | 3/2003 | Fecteau et al. |
| 6,557,556 B2 | 5/2003 | Kwok et al. |
| 6,561,188 B1 | 5/2003 | Ellis |
| 6,561,190 B1 | 5/2003 | Kwok |
| 6,561,191 B1 | 5/2003 | Kwok |
| 6,561,192 B2 | 5/2003 | Palmer |
| 6,561,193 B1 | 5/2003 | Noble |
| 6,571,798 B1 | 6/2003 | Thornton |
| 6,579,267 B2 | 6/2003 | Lynch et al. |
| 6,581,601 B2 | 6/2003 | Ziaee |
| 6,581,602 B2 | 6/2003 | Kwok et al. |
| 6,584,975 B1 | 7/2003 | Taylor |
| 6,595,214 B1 | 7/2003 | Hecker et al. |
| 6,595,215 B2 | 7/2003 | Wood |
| 6,607,516 B2 | 8/2003 | Cinelli et al. |
| 6,615,830 B1 | 9/2003 | Serowski et al. |
| 6,615,832 B1 | 9/2003 | Chen |
| 6,626,177 B1 | 9/2003 | Ziaee |
| 6,627,289 B1 | 9/2003 | Dilnik et al. |
| 6,631,718 B1 | 10/2003 | Lovell |
| 6,634,358 B2 | 10/2003 | Kwok et al. |
| 6,637,434 B2 | 10/2003 | Noble |
| 6,644,315 B2 | 11/2003 | Ziaee |
| 6,651,663 B2 | 11/2003 | Barnett et al. |
| D484,237 S | 12/2003 | Lang et al. |
| 6,655,385 B1 | 12/2003 | Curti et al. |
| 6,663,600 B2 | 12/2003 | Bierman et al. |
| 6,669,712 B1 | 12/2003 | Cardoso |
| D485,905 S | 1/2004 | Moore et al. |
| 6,679,257 B1 | 1/2004 | Robertson et al. |
| 6,679,261 B2 | 1/2004 | Lithgow |
| 6,679,265 B2 | 1/2004 | Strickland et al. |
| 6,691,707 B1 | 2/2004 | Gunaratnam et al. |
| 6,691,708 B2 | 2/2004 | Kwok et al. |
| 6,701,535 B2 | 3/2004 | Dobbie et al. |
| 6,701,926 B2 | 3/2004 | Olsen et al. |
| 6,701,927 B2 | 3/2004 | Kwok et al. |
| 6,710,099 B2 | 3/2004 | Cinelli et al. |
| 6,712,072 B1 | 3/2004 | Lang |
| 6,729,333 B2 | 5/2004 | Barnett et al. |
| D492,992 S | 7/2004 | Guney et al. |
| D493,521 S | 7/2004 | Guney |
| 6,766,800 B2 | 7/2004 | Chu et al. |
| 6,766,817 B2 | 7/2004 | da Silva |
| 6,772,760 B2 | 8/2004 | Frater et al. |
| 6,776,162 B2 | 8/2004 | Wood |
| 6,776,163 B2 | 8/2004 | Dougill et al. |
| 6,789,543 B2 | 9/2004 | Cannon |
| 6,796,308 B2 | 9/2004 | Gunaratnam et al. |
| 6,805,117 B1 | 10/2004 | Ho et al. |
| 6,807,967 B2 | 10/2004 | Wood |
| 6,817,362 B2 | 11/2004 | Gelinas et al. |
| 6,820,617 B2 | 11/2004 | Robertson et al. |
| 6,823,865 B2 | 11/2004 | Drew et al. |
| 6,823,869 B2 | 11/2004 | Raje et al. |
| 6,834,650 B2 | 12/2004 | Fini |
| 6,851,425 B2 | 2/2005 | Jaffre |
| 6,851,428 B2 | 2/2005 | Dennis |
| 6,851,429 B2 | 2/2005 | Bishop |
| 6,860,269 B2 | 3/2005 | Kwok et al. |
| 6,860,270 B2 | 3/2005 | Sniadach |
| 6,871,649 B2 | 3/2005 | Kwok et al. |
| 6,892,729 B2 | 5/2005 | Smith et al. |
| 6,895,965 B2 | 5/2005 | Scarberry et al. |
| 6,907,882 B2 | 6/2005 | Ging |
| 6,914,091 B2 | 7/2005 | Donald et al. |
| 6,918,404 B2 | 7/2005 | Dias da Silva |
| 6,926,004 B2 | 8/2005 | Schumacher |
| 6,938,620 B2 | 9/2005 | Payne, Jr. |
| 6,959,710 B2 | 11/2005 | Barnett et al. |
| 6,968,844 B2 | 11/2005 | Liland |
| 6,972,003 B2 | 12/2005 | Bierman et al. |
| 6,986,352 B2 | 1/2006 | Frater et al. |
| 6,997,177 B2 | 2/2006 | Wood |
| 7,000,614 B2 | 2/2006 | Lang et al. |
| 7,007,696 B2 | 3/2006 | Palkon et al. |
| 7,011,090 B2 | 3/2006 | Drew et al. |
| 7,018,362 B2 | 3/2006 | Bierman et al. |
| 7,040,321 B2 | 5/2006 | Goebel |
| 7,052,127 B2 | 5/2006 | Harrison |
| 7,059,326 B2 | 6/2006 | Heidmann et al. |
| 7,066,586 B2 | 6/2006 | da Silva |
| 7,069,932 B2 | 7/2006 | Eaton et al. |
| 7,076,282 B2 | 7/2006 | Munro et al. |
| 7,076,822 B2 | 7/2006 | Pearce |
| 7,080,645 B2 | 7/2006 | Genger et al. |
| 7,093,599 B2 | 8/2006 | Chen |
| 7,100,610 B2 | 9/2006 | Biener et al. |
| 7,101,359 B2 | 9/2006 | Kline et al. |
| 7,107,989 B2 | 9/2006 | Frater et al. |
| 7,114,497 B2 | 10/2006 | Aylsworth et al. |
| 7,146,976 B2 | 12/2006 | McKown |
| 7,152,599 B2 | 12/2006 | Thomas |
| 7,152,601 B2 | 12/2006 | Barakat et al. |
| 7,441,618 B2 | 12/2006 | Lubke et al. |
| 7,178,525 B2 | 2/2007 | Matula, Jr. et al. |
| 7,185,652 B2 | 3/2007 | Gunaratnam et al. |
| 7,191,781 B2 | 3/2007 | Wood |
| 7,207,328 B1 | 4/2007 | Altemus |
| 7,207,335 B2 | 4/2007 | Kwok et al. |
| 7,210,481 B1 | 5/2007 | Lovell et al. |

| Patent No. | Date | Inventor |
|---|---|---|
| 7,216,647 B2 | 5/2007 | Lang et al. |
| 7,237,551 B2 | 7/2007 | Ho et al. |
| 7,243,723 B2 | 7/2007 | Surjaatmadja |
| D550,836 S | 9/2007 | Chandran et al. |
| D552,733 S | 10/2007 | Criscuolo et al. |
| 7,285,255 B2 | 10/2007 | Kadlec et al. |
| 7,302,950 B2 | 12/2007 | Berthon-Jones et al. |
| 7,308,895 B2 | 12/2007 | Wixey et al. |
| 7,318,437 B2 | 1/2008 | Gunaratnam |
| 7,318,439 B2 | 1/2008 | Raje et al. |
| 7,320,323 B2 | 1/2008 | Lang et al. |
| 7,341,060 B2 | 3/2008 | Ging et al. |
| 7,353,826 B2 | 4/2008 | Sleeper et al. |
| 7,461,656 B2 | 12/2008 | Gunaratnam et al. |
| 7,470,256 B2 | 12/2008 | Lampropoulos et al. |
| 7,481,220 B2 | 1/2009 | Meyer et al. |
| 7,487,772 B2 | 2/2009 | Ging et al. |
| 7,503,327 B2 | 3/2009 | Gunaratnam |
| 7,509,958 B2 | 3/2009 | Amarasinghe et al. |
| 7,520,869 B2 | 4/2009 | Lampropoulos et al. |
| 7,523,754 B2 | 4/2009 | Lithgow |
| 7,562,658 B2 | 7/2009 | Madaus et al. |
| 7,614,400 B2 | 11/2009 | Lithgow et al. |
| 7,614,401 B2 | 11/2009 | Thompson |
| 7,621,274 B2 | 11/2009 | Sprinkle et al. |
| 7,624,735 B2 | 12/2009 | Ho et al. |
| 7,640,934 B2 | 1/2010 | Zollinger et al. |
| 7,654,263 B2 | 2/2010 | Lang et al. |
| 7,658,189 B2 | 2/2010 | Davidson et al. |
| 7,665,464 B2 | 2/2010 | Kopacko et al. |
| 7,699,808 B2 | 4/2010 | Marrs et al. |
| 7,703,457 B2 | 4/2010 | Barnett et al. |
| 7,708,017 B2 | 5/2010 | Davidson |
| 7,743,767 B2 | 6/2010 | Ging et al. |
| 7,762,259 B2 | 7/2010 | Gunaratnam |
| 7,775,209 B2 | 8/2010 | Biener et al. |
| 7,779,832 B1 | 8/2010 | Ho |
| 7,798,144 B2 | 9/2010 | Kwok et al. |
| 7,814,911 B2 | 10/2010 | Bordewick et al. |
| 7,819,119 B2 | 10/2010 | Ho |
| 7,827,990 B1 | 11/2010 | Melidis et al. |
| 7,841,345 B2 | 11/2010 | Guney et al. |
| 7,856,980 B2 | 12/2010 | Lang et al. |
| 7,856,982 B2 | 12/2010 | Matula, Jr. et al. |
| 7,861,715 B2 | 1/2011 | Jones et al. |
| 7,874,293 B2 | 1/2011 | Gunaratnam et al. |
| 7,878,199 B2 | 2/2011 | Ging et al. |
| 7,900,631 B2 | 3/2011 | Persson |
| 7,900,635 B2 | 3/2011 | Gunaratnam et al. |
| 7,931,024 B2 | 4/2011 | Ho et al. |
| 7,958,893 B2 | 6/2011 | Lithgow et al. |
| 7,967,013 B2 | 6/2011 | Ging et al. |
| 7,967,014 B2 | 6/2011 | Heidmann et al. |
| 7,971,590 B2 | 7/2011 | Frater et al. |
| 7,992,559 B2 | 8/2011 | Lang et al. |
| 7,997,267 B2 | 8/2011 | Ging et al. |
| 8,042,538 B2 | 10/2011 | Ging et al. |
| 8,042,541 B2 | 10/2011 | Amarasinghe et al. |
| 8,042,542 B2 | 10/2011 | Ging et al. |
| 8,042,546 B2 | 10/2011 | Gunaratnam et al. |
| 8,051,850 B2 | 11/2011 | Kwok et al. |
| 8,091,553 B2 | 1/2012 | Bordewick et al. |
| 8,096,301 B2 | 1/2012 | Smith et al. |
| 8,136,524 B2 | 3/2012 | Ging et al. |
| 8,136,525 B2 | 3/2012 | Lubke et al. |
| 8,186,352 B2 | 5/2012 | Gunaratnam et al. |
| 8,210,180 B2 | 7/2012 | Gunaratnam |
| 8,220,459 B2 | 7/2012 | Davidson et al. |
| 8,297,283 B2 | 10/2012 | Hitchcock et al. |
| 8,397,728 B2 | 3/2013 | D'Souza et al. |
| 2001/0020474 A1 | 9/2001 | Hecker et al. |
| 2002/0020416 A1 | 2/2002 | Namey |
| 2002/0029780 A1 | 3/2002 | Frater et al. |
| 2002/0046755 A1 | 4/2002 | Devoss |
| 2002/0066452 A1 | 6/2002 | Kessler et al. |
| 2002/0069872 A1 | 6/2002 | Gradon et al. |
| 2002/0124849 A1 | 9/2002 | Billette de Villemeur |
| 2002/0143296 A1 | 10/2002 | Russo |
| 2002/0157673 A1 | 10/2002 | Kessler et al. |
| 2002/0174868 A1 | 11/2002 | Kwok et al. |
| 2003/0019495 A1 | 1/2003 | Palkon et al. |
| 2003/0062048 A1 | 4/2003 | Gradon et al. |
| 2003/0089373 A1 | 5/2003 | Gradon et al. |
| 2003/0168063 A1 | 9/2003 | Gambone et al. |
| 2003/0196656 A1 | 10/2003 | Moore et al. |
| 2003/0196658 A1 | 10/2003 | Ging et al. |
| 2004/0025883 A1* | 2/2004 | Eaton et al. ............ 128/206.27 |
| 2004/0094157 A1 | 5/2004 | Dantanarayana et al. |
| 2004/0106891 A1 | 6/2004 | Langan et al. |
| 2004/0111104 A1 | 6/2004 | Schein et al. |
| 2004/0112384 A1 | 6/2004 | Lithgow et al. |
| 2004/0112385 A1 | 6/2004 | Drew et al. |
| 2004/0127856 A1 | 7/2004 | Johnson |
| 2004/0177850 A1 | 9/2004 | Gradon et al. |
| 2004/0182398 A1 | 9/2004 | Sprinkle et al. |
| 2004/0211428 A1 | 10/2004 | Jones |
| 2004/0226566 A1 | 11/2004 | Gunaratnam et al. |
| 2005/0051171 A1 | 3/2005 | Booth |
| 2005/0051176 A1 | 3/2005 | Riggins |
| 2005/0056286 A1 | 3/2005 | Huddart et al. |
| 2005/0061326 A1 | 3/2005 | Payne, Jr. |
| 2005/0098183 A1 | 5/2005 | Nash et al. |
| 2005/0150495 A1 | 7/2005 | Rittner et al. |
| 2005/0155604 A1 | 7/2005 | Ging et al. |
| 2005/0211252 A1 | 9/2005 | Lang et al. |
| 2005/0241644 A1 | 11/2005 | Gunaratnam et al. |
| 2006/0076017 A1* | 4/2006 | Walker et al. ............ 128/205.24 |
| 2006/0124131 A1 | 6/2006 | Chandran et al. |
| 2006/0137690 A1 | 6/2006 | Gunaratnam et al. |
| 2006/0174887 A1 | 8/2006 | Chandran et al. |
| 2006/0207597 A1 | 9/2006 | Wright |
| 2006/0213520 A1 | 9/2006 | Frater et al. |
| 2006/0272646 A1 | 12/2006 | Ho et al. |
| 2006/0283461 A1 | 12/2006 | Lubke et al. |
| 2007/0044804 A1 | 3/2007 | Matula, Jr. et al. |
| 2007/0137653 A1 | 6/2007 | Wood |
| 2007/0144525 A1 | 6/2007 | Davidson et al. |
| 2007/0215161 A1 | 9/2007 | Frater et al. |
| 2007/0221226 A1 | 9/2007 | Hansen et al. |
| 2007/0272249 A1 | 11/2007 | Chandran et al. |
| 2007/0282272 A1 | 12/2007 | Bannon et al. |
| 2008/0004573 A1 | 1/2008 | Kaufmann et al. |
| 2008/0006277 A1 | 1/2008 | Worboys et al. |
| 2008/0047560 A1 | 2/2008 | Veliss et al. |
| 2008/0060649 A1 | 3/2008 | Veliss et al. |
| 2008/0065022 A1 | 3/2008 | Kyvik et al. |
| 2008/0110464 A1 | 5/2008 | Davidson et al. |
| 2008/0110469 A1 | 5/2008 | Weinberg |
| 2008/0178875 A1 | 7/2008 | Henry |
| 2008/0178886 A1* | 7/2008 | Lieberman et al. ...... 128/206.24 |
| 2008/0200880 A1 | 8/2008 | Kyvik et al. |
| 2008/0257354 A1 | 10/2008 | Davidson et al. |
| 2008/0302365 A1 | 12/2008 | Cohen et al. |
| 2008/0314389 A1 | 12/2008 | Thomas et al. |
| 2009/0044808 A1 | 2/2009 | Guney et al. |
| 2009/0126739 A1 | 5/2009 | Ng et al. |
| 2009/0139526 A1 | 6/2009 | Melidis et al. |
| 2009/0139527 A1 | 6/2009 | Ng et al. |
| 2009/0173343 A1 | 7/2009 | Omura et al. |
| 2009/0217929 A1 | 9/2009 | Kwok et al. |
| 2009/0223518 A1 | 9/2009 | Kwok et al. |
| 2009/0223521 A1 | 9/2009 | Howard et al. |
| 2010/0000534 A1 | 1/2010 | Kooij et al. |
| 2010/0000543 A1 | 1/2010 | Berthon-Jones et al. |
| 2010/0018534 A1 | 1/2010 | Veliss et al. |
| 2010/0089401 A1 | 4/2010 | Lang et al. |
| 2010/0132717 A1 | 6/2010 | Davidson et al. |
| 2010/0192955 A1 | 8/2010 | Biener et al. |
| 2010/0282265 A1 | 11/2010 | Melidis et al. |
| 2010/0300447 A1 | 12/2010 | Biener et al. |
| 2010/0319700 A1 | 12/2010 | Ng et al. |
| 2011/0030692 A1 | 2/2011 | Jones et al. |
| 2011/0056497 A1 | 3/2011 | Scheiner et al. |
| 2011/0220110 A1 | 9/2011 | Frater et al. |
| 2011/0220114 A1 | 9/2011 | Lithgow et al. |
| 2011/0226254 A1 | 9/2011 | Lang et al. |
| 2011/0259337 A1 | 10/2011 | Hitchcock et al. |
| 2012/0138063 A1 | 6/2012 | Eves et al. |

| | | |
|---|---|---|
| 2012/0174928 A1 | 7/2012 | Raje et al. |
| 2012/0266886 A1 | 10/2012 | Davidson et al. |
| 2013/0037033 A1 | 2/2013 | Hitchcock et al. |
| 2013/0081628 A1 | 4/2013 | Davidson et al. |
| 2013/0081629 A1 | 4/2013 | Davidson et al. |
| 2013/0081630 A1 | 4/2013 | Davidson et al. |
| 2013/0081631 A1 | 4/2013 | Davidson et al. |
| 2013/0081632 A1 | 4/2013 | Davidson et al. |
| 2013/0086795 A1 | 4/2013 | Davidson et al. |
| 2013/0086796 A1 | 4/2013 | Davidson et al. |
| 2013/0087147 A1 | 4/2013 | Davidson et al. |
| 2013/0087148 A1 | 4/2013 | Davidson et al. |
| 2013/0087149 A1 | 4/2013 | Davidson et al. |
| 2013/0092168 A1 | 4/2013 | Davidson et al. |
| 2013/0092170 A1 | 4/2013 | Davidson et al. |

FOREIGN PATENT DOCUMENTS

| | | |
|---|---|---|
| AU | 95/16178 | 7/1995 |
| AU | 94/59430 | 10/1995 |
| AU | 95/32914 | 2/1996 |
| AU | 96/51130 | 10/1996 |
| AU | 97/41018 | 4/1998 |
| AU | 98/89312 | 1/1999 |
| AU | 2005100738 | 11/2005 |
| AU | 2006/00031 | 1/2006 |
| CA | 618807 | 4/1961 |
| CA | 623129 | 7/1961 |
| CA | 1039144 | 9/1978 |
| CN | 1219883 A | 6/1999 |
| CN | 2464353 | 12/2001 |
| CN | 1735439 | 2/2006 |
| DE | 185 017 | 5/1907 |
| DE | 284 800 | 11/1913 |
| DE | 459 104 | 4/1928 |
| DE | 701 690 | 1/1941 |
| DE | 30 11 900 | 10/1980 |
| DE | 146 688 | 1/1981 |
| DE | 30 15 279 | 10/1981 |
| DE | 31 49 449 | 10/1982 |
| DE | 159 396 | 3/1983 |
| DE | 33 45 067 | 6/1984 |
| DE | 37 07 952 | 3/1987 |
| DE | 35 37 507 | 4/1987 |
| DE | 35 39 073 | 5/1987 |
| DE | 37 19 009 | 12/1988 |
| DE | 39 27 038 | 2/1991 |
| DE | 40 04 157 | 4/1991 |
| DE | 42 12 259 | 1/1993 |
| DE | 42 33 448 | 4/1993 |
| DE | 43 43 205 | 6/1995 |
| DE | 195 48 380 | 7/1996 |
| DE | 196 03 949 | 8/1997 |
| DE | 297 15 718 | 10/1997 |
| DE | 197 35 359 | 1/1998 |
| DE | 297 23 101 | 7/1998 |
| DE | 197 03 526 | 8/1998 |
| DE | 298 10 846 | 8/1998 |
| DE | 198 17 332 | 1/1999 |
| DE | 198 07 961 | 8/1999 |
| DE | 198 08 105 | 9/1999 |
| DE | 198 40 760 | 3/2000 |
| DE | 200 05 346 | 5/2000 |
| DE | 299 23 141 | 5/2000 |
| DE | 200 17 940 | 2/2001 |
| DE | 199 44 242 | 3/2001 |
| DE | 199 54 517 | 6/2001 |
| DE | 100 02 571 | 7/2001 |
| DE | 199 62 515 | 7/2001 |
| DE | 100 45 183 | 5/2002 |
| DE | 102 13 905 | 10/2002 |
| DE | 10 2004 055 433 | 11/2004 |
| DE | 103 31 837 | 1/2005 |
| DE | 20 2004 018 108 | 2/2005 |
| DE | 103 38 169 | 3/2005 |
| EP | 0 054 154 | 6/1982 |
| EP | 0 252 052 | 1/1988 |
| EP | 0 264 772 | 4/1988 |
| EP | 0 288 937 | 11/1988 |
| EP | 0 334 555 | 9/1989 |
| EP | 0 386 605 | 9/1990 |
| EP | 0 427 474 | 5/1991 |
| EP | 0 462 701 | 12/1991 |
| EP | 0 466 960 | 1/1992 |
| EP | 0 303 090 B1 | 4/1992 |
| EP | 0 549 299 | 6/1993 |
| EP | 0 602 424 | 6/1994 |
| EP | 0 608 684 | 8/1994 |
| EP | 0 658 356 | 6/1995 |
| EP | 0 697 225 | 2/1996 |
| EP | 0 178 925 A2 | 4/1996 |
| EP | 0 747 078 | 12/1996 |
| EP | 0 776 679 | 6/1997 |
| EP | 0 821 978 | 2/1998 |
| EP | 0 853 962 | 7/1998 |
| EP | 1 027 905 | 8/2000 |
| EP | 1 057 494 | 12/2000 |
| EP | 1 099 452 | 5/2001 |
| EP | 1 118 346 | 7/2001 |
| EP | 1 163 923 | 12/2001 |
| EP | 1 205 205 | 5/2002 |
| EP | 1 258 266 | 11/2002 |
| EP | 1 356 843 | 10/2003 |
| EP | 1 360 971 | 11/2003 |
| EP | 1 481 702 | 12/2004 |
| EP | 2 471 566 | 7/2012 |
| EP | 2 471 567 | 7/2012 |
| FR | 780018 | 4/1935 |
| FR | 2 574 657 | 6/1986 |
| FR | 2 658 725 | 8/1991 |
| FR | 2 720 280 | 12/1995 |
| FR | 2 749 176 | 12/1997 |
| FR | 2 823 122 | 10/2002 |
| GB | 532 214 | 1/1941 |
| GB | 649 689 | 1/1951 |
| GB | 823 887 | 11/1959 |
| GB | 880942 | 10/1961 |
| GB | 1 395 391 | 5/1975 |
| GB | 1 467 828 | 3/1977 |
| GB | 2 145 335 | 3/1985 |
| GB | 2 147 506 | 5/1985 |
| GB | 2 164 569 | 3/1986 |
| GB | 2 176 404 | 12/1986 |
| GB | 2 186 801 | 8/1987 |
| GB | 2 267 648 | 12/1993 |
| GB | 2 368 533 | 5/2002 |
| GB | 2 385 533 | 5/2003 |
| JP | S39-13991 | 7/1964 |
| JP | S51-142793 | 11/1976 |
| JP | H03-007173 | 1/1991 |
| JP | H09-216240 | 8/1997 |
| JP | H11-000397 | 1/1999 |
| JP | H11-104256 | 4/1999 |
| JP | H11-508159 | 7/1999 |
| JP | 2000-279520 | 10/2000 |
| JP | 2000-325481 | 11/2000 |
| JP | 2000-515784 | 11/2000 |
| JP | 2002-028240 | 4/2002 |
| JP | 2002-543943 | 12/2002 |
| JP | 2003-175106 | 6/2003 |
| JP | 2003-535657 | 12/2003 |
| JP | 2004-000570 | 1/2004 |
| JP | 2005-337371 | 12/2005 |
| JP | 3802872 | 7/2006 |
| JP | 2008/501438 | 1/2008 |
| WO | WO 80/01044 | 5/1980 |
| WO | WO 82/03548 | 10/1982 |
| WO | WO 86/06969 | 12/1986 |
| WO | WO 87/01950 | 4/1987 |
| WO | WO 91/03277 | 3/1991 |
| WO | WO 92/15353 | 9/1992 |
| WO | WO 92/20392 | 11/1992 |
| WO | WO 92/20395 | 11/1992 |
| WO | WO 93/01854 | 2/1993 |
| WO | WO 93/24169 | 12/1993 |
| WO | WO 94/02190 | 2/1994 |
| WO | WO 94/16759 | 8/1994 |
| WO | WO 94/20051 | 9/1994 |
| WO | WO 95/02428 | 1/1995 |

| | | |
|---|---|---|
| WO | WO 96/17643 | 6/1996 |
| WO | WO 96/25983 | 8/1996 |
| WO | WO 96/28207 | 9/1996 |
| WO | WO 96/39206 | 12/1996 |
| WO | WO 97/00092 | 1/1997 |
| WO | WO 97/07847 | 3/1997 |
| WO | WO 97/09090 | 3/1997 |
| WO | WO 97/41911 | 11/1997 |
| WO | WO 98/03145 | 1/1998 |
| WO | WO 98/04310 | 2/1998 |
| WO | WO 98/11930 | 3/1998 |
| WO | WO 98/12965 | 4/1998 |
| WO | WO 98/18514 | 5/1998 |
| WO | WO 98/23305 | 6/1998 |
| WO | WO 98/24499 | 6/1998 |
| WO | WO 98/26829 | 6/1998 |
| WO | WO 98/26830 | 6/1998 |
| WO | WO 98/34665 | 8/1998 |
| WO | WO 98/48878 | 11/1998 |
| WO | WO 99/16327 | 4/1999 |
| WO | WO 99/25410 | 5/1999 |
| WO | WO 99/43375 | 9/1999 |
| WO | WO 99/58181 | 11/1999 |
| WO | WO 99/61088 | 12/1999 |
| WO | WO 99/65554 | 12/1999 |
| WO | WO 00/20072 | 4/2000 |
| WO | WO 00/21600 | 4/2000 |
| WO | WO 00/35525 | 6/2000 |
| WO | WO 00/38772 | 7/2000 |
| WO | WO 00/50121 | 8/2000 |
| WO | WO 00/57942 | 10/2000 |
| WO | WO 00/69521 | 11/2000 |
| WO | WO 00/72905 | 12/2000 |
| WO | WO 00/74758 | 12/2000 |
| WO | WO 00/76568 | 12/2000 |
| WO | WO 00/78381 | 12/2000 |
| WO | WO 00/78384 | 12/2000 |
| WO | WO 01/62326 | 8/2001 |
| WO | WO 01/95965 | 12/2001 |
| WO | WO 01/97892 | 12/2001 |
| WO | WO 01/97893 | 12/2001 |
| WO | WO 02/11804 | 2/2002 |
| WO | WO 02/32491 | 4/2002 |
| WO | WO 02/38221 | 5/2002 |
| WO | WO 02/45784 | 6/2002 |
| WO | WO 03/005931 | 1/2003 |
| WO | WO 03/059427 | 7/2003 |
| WO | WO 03/082406 | 10/2003 |
| WO | WO 03/090827 | 11/2003 |
| WO | WO 03/105921 | 12/2003 |
| WO | WO 2004/007010 | 1/2004 |
| WO | WO 2004/022144 | 3/2004 |
| WO | WO 2004/022145 | 3/2004 |
| WO | WO 2004/022146 | 3/2004 |
| WO | WO 2004/022147 | 3/2004 |
| WO | WO 2004/041342 | 5/2004 |
| WO | WO 2004/073778 | 9/2004 |
| WO | WO 2004/078228 | 9/2004 |
| WO | WO 2004/078230 | 9/2004 |
| WO | WO 2004/096332 | 11/2004 |
| WO | WO 2005/002656 | 1/2005 |
| WO | WO 2005/018523 | 3/2005 |
| WO | WO 2005/021075 | 3/2005 |
| WO | WO 2005/028010 | 3/2005 |
| WO | WO 2005/053781 | 6/2005 |
| WO | WO 2005/063326 | 7/2005 |
| WO | WO 2005/063328 | 7/2005 |
| WO | WO 2005/086943 | 9/2005 |
| WO | WO 2005/094928 | 10/2005 |
| WO | WO 2005/099801 | 10/2005 |
| WO | WO 2005/110220 | 11/2005 |
| WO | WO 2005/118040 | 12/2005 |
| WO | WO 2005/123166 | 12/2005 |
| WO | WO 2006/000046 | 1/2006 |
| WO | WO 2006/014630 | 2/2006 |
| WO | WO 2006/052653 | 5/2006 |
| WO | WO 2006/069345 | 6/2006 |
| WO | WO 2006/069415 | 7/2006 |
| WO | WO 2006/074513 | 7/2006 |
| WO | WO2006/074514 | * 7/2006 |
| WO | WO 2006/074515 | 7/2006 |
| WO | WO 2006/074516 | 7/2006 |
| WO | WO 2006/099658 | 9/2006 |
| WO | WO 2006/102707 | 10/2006 |
| WO | WO 2006/130903 | 12/2006 |
| WO | WO 2006/138416 | 12/2006 |
| WO | WO 2007/009182 | 1/2007 |
| WO | WO 2007/041751 | 4/2007 |
| WO | WO 2007/041786 | 4/2007 |
| WO | WO 2007/048174 | 5/2007 |
| WO | WO 2007/053878 | 5/2007 |
| WO | WO 2007/143772 | 12/2007 |
| WO | WO 2007/143792 | 12/2007 |
| WO | WO 2007/145534 | 12/2007 |
| WO | WO 2008/011682 | 1/2008 |
| WO | WO 2008/011683 | 1/2008 |
| WO | WO 2008/040050 | 4/2008 |
| WO | WO 2008/070929 | 6/2008 |
| WO | WO 2009/026627 | 3/2009 |
| WO | WO 2009/052560 | 4/2009 |
| WO | WO 2009/062265 | 5/2009 |
| WO | WO 2009/108994 | 9/2009 |
| WO | WO 2009/108995 | 9/2009 |
| WO | WO 2009/109004 | 9/2009 |
| WO | WO 2010/028425 | 3/2010 |
| WO | WO 2010/066004 | 6/2010 |
| WO | WO 2011/060479 | 5/2011 |
| WO | WO 2013/057647 | 4/2013 |
| WO | WO 2013/061260 | 5/2013 |

OTHER PUBLICATIONS

Ng et al., U.S. Appl. No. 12/736,024, filed Sep. 2, 2010.
Ng et al., U.S. Appl. No. 13/745,077, filed Jan. 18, 2013.
Ng et al., U.S. Appl. No. 13/747,701, filed Jan. 23, 2013.
Photographs of Weinmann Mask, acquired prior to 1998, 7 pages.
Adam J. Singer MD et al. "The Cyanoacrylate Topical Skin Adhesives," American Journal of Emergency Medicine, vol. 26, 2008, pp. 490-496.
Australian Appln. No. 2005253641—Examiner's First Report, dated Apr. 20, 2010.
Australian Appln. No. 2005253641—Examiner's Report, dated Aug. 18, 2011.
Australian Appln. No. 2006206040—Examination Report, dated Jun. 27, 2012.
Australian Appln. No. 2010251884—Examination Report, dated Jul. 27. 2012.
Australian Appln. No. PCT/AU2009/000214—International Search Report, dated May 18, 2009.
Chinese Appln. No. 200480011911.9—Office Action (w/English translation), dated Jun. 24, 2010.
Chinese Appln. No. 200580020203.6—Office Action (w/English translation), dated Jun. 1, 2010.
Chinese Appln. No. 200580020203.6—Office Action (w/English translation), dated Jul. 6, 2011.
Chinese Appln. No. 200580020203.6—Office Action (w/English translation), dated Dec. 23, 2011.
Chinese Appln. No. 200580020203.6—Office Action (w/English translation), dated Apr. 18, 2012.
Chinese Appln. No. 200680002169.4—Office Action (w/English translation), dated Mar. 23, 2010.
Chinese Appln. No. 200680002169.4—Third Office Action (w/English translation), dated Nov. 11, 2010.
Chinese Appln. No. 200810109270.0—Office Action (w/English translation), dated Oct. 19, 2011.
Chinese Appln. No. 200810109270.0—Office Action (w/English translation), dated Jun. 27, 2012.
Chinese Appln. No. 200910223650.1—Office Action (w/English translation), dated Mar. 29, 2012.
Chinese Appln. No. 201010000226.3—Office Action (w/English translation), dated Apr. 26, 2012.
Chinese Appln. No. 201010517066.X—Office Action (w/English translation), dated Nov. 10, 2011.
ComfortLite™, Respironics, http://comfortlite.respironics.com, before applicants' filing date.

ComfortLite™ 2, Respironics, http://comfortlite2.respironics.com, before applicants' filing date.

"Ear Loop Face Mask", before applicants' filing date.

European Appln. No. EP 01944732.5—Office Action, dated Nov. 27, 2009.

European Appln. No. EP 02714190.2—Search Report, dated Jul. 11, 2006.

European Appln. No. EP 03793493.2—Supplementary Search Report, dated Dec. 2, 2009.

European Appln. No. EP 03793493.2—Office Action, dated Mar. 18, 2011.

European Appln. No. EP 03810331.3—Supplementary Search Report, dated Dec. 18, 2009.

European Appln. No. EP 04730413.4—Supplementary Search Report, dated Sep. 29, 2009.

European Appln. No. EP 04802114.1—Supplementary Search Report, dated Apr. 27, 2009.

European Appln. No. EP 04802133.1—Supplementary Search Report, dated Sep. 8, 2009.

European Appln. No. EP 04802133.1—Office Action, dated Dec. 22, 2009.

European Appln. No. EP 05746824.1—Supplementary Search Report, dated Dec. 17, 2009.

European Appln. No. EP 05749447.8—Supplementary Search Report, dated Dec. 8, 2009.

European Appln. No. EP 06704287.9—Supplementary Search Report, dated Oct. 6, 2009.

European Appln. No. EP 06704287.9—Office Action, dated Jul. 18, 2011.

European Appln. No. EP 07784697.0—Search Report, dated Jul. 27, 2009.

European Appln. No. EP 07845378.4—Search Report, dated Dec. 1, 2009.

European Appln. No. EP 08154854.7—Extended Search Report, dated Nov. 27, 2008.

European Appln. No. EP 08154854.7—Examination Report, dated Jul. 1, 2011.

European Appln. No. EP 08161249.1—Extended Search Report, dated Mar. 19, 2009.

European Appln. No. EP 08161868.8—Search Report, dated Sep. 23, 2008.

European Appln. No. EP 09003544.5—Search Report, dated Jun. 2, 2009.

European Appln. No. EP 09161984.1—Extended Search Report, dated Sep. 3, 2009.

European Appln. No. EP 09178736.6—Search Report, dated Apr. 19, 2010.

European Appln. No. EP 10181516.5—Search Report, dated Jun. 13, 2012.

European Appln. No. EP 10182015.7—Search Report, dated Jun. 15, 2012.

European Appln. No. EP 11174401.7—Search Report, dated Oct. 20, 2011.

European Appln. No. EP 11174407.4—Extended Search Report. dated Oct. 20, 2011.

European Appln. No. EP 12154923.2—Extended Search Report, dated Jun. 1, 2012.

European Appln. No. EP 12154926.5—Extended Search Report, dated Jun. 6, 2012.

European Appln. No. EP 12165749.8—Extended Search Report, dated Oct. 10, 2012.

European Appln. No. EP 12165751.4—Extended Search Report, dated Oct. 8, 2012.

Fisher and Paykel Col.—Product Family—http://www.fphcare.com/osa/products.asp/, before applicants' filing date.

German Patent No. 101 51 984—Decision from Opposition hearing by Weinmann (w/English translation), dated Dec. 6, 2007.

Hans Rudolph, Inc.—Mask Products—http://www.rudolphkc.com/products.php?category=MASKS, before applicants' filing date.

"If You Hate CPAP! You Need CPAP Pro®," www.cpappro.com, before applicants' filing date.

Japanese Appln. No. 2003-537718 Office Action (w/English translation), dated Oct. 7, 2008.

Japanese Appln. No. 2003-559587—Office Action (w/English translation), dated Mar. 17, 2009.

Japanese Appln. No. 2005-004072—Office Action (w/English translation), dated Sep. 24, 2009.

Japanese Appln. No. 2005-337371—Reasons for Rejection (w/English translation), dated Feb. 22, 2011.

Japanese Appln. No. 2005-337371—Final Office Action (w/English translation), dated Jan. 31, 2012.

Japanese Appln. No. 2006-504029—Office A545843ction (w/English translation), dated Nov. 10, 2009.

Japanese Appln. No. 2006-545843—Notice of Reasons for Rejection (w/English translation), dated Jun. 7, 2011.

Japanese Appln. No. 2007-515732—Office Action (w/English translation), dated Aug. 24, 2010.

Japanese Appln. No. 2007-515732—Office Action (w/English translation), dated Aug. 16, 2011.

Japanese Appln. No. 2007-515732—Office Action (w/English translation), dated Jun. 12, 2012.

Japanese Appln. No. 2007-550636—Office Action (w/English translation), dated Mar. 18, 2011.

Japanese Appln. No. 2007-550636—Office Action (w/English translation), dated Mar. 21, 2012.

Japanese Appln. No. 2007-550636—Notice of Allowance, dated Jul. 10, 2012.

Japanese Appln. No. 2009-140433—Office Action (w/English translation), dated Aug. 20, 2011.

Japanese Appln. No. 2009-140433—Notice of Allowance, dated Sep. 4, 2012.

Japanese Appln. No. 2010-195597—Office Action (w/English translation), dated Jun. 12, 2012.

Japanese Appln. No. 2010-214485—Office Action (w/English translation), dated Jun. 12, 2012.

Japanese Appln. No. 2010-268127—Notice of Reasons for Rejection (w/English translation), dated Jul. 10, 2012.

Japanese Appln. No. 2011-038110—Office Action (w/English translation), dated Aug. 14, 2012.

Japanese Appln. No. S52-164619—English translation of Figure 1, Dec. 1977.

Joel W. Beam, "Tissue Adhesives for Simple Traumatic Lacerations," Journal of Athletic Training, 2008, vol. 43, No. 2, pp. 222-224.

JP 11-000397A Machine Translation, provided by the Japanese Patent Office, Jan. 6, 2009, full document.

Laurent Brochard, "Pressure Support Ventilation," Chapter 9. Part IV—Conventional Methods of Ventilator Support, pp. 239-257, 1994.

Mask 1 Photographs, Respironics Inc., Reusable Full Mask (small) Part #452033 Lot #951108, before applicants' filing date.

Mask 2 Photographs, Puritan—Bennett, Adam Curcuit, Shell Part #231700, Swivel Part #616329-00. Pillows (medium) Part #616324, before applicants' filing date.

Mask 3 Photographs, DeVilbiss Healthcare Inc., Devilbiss Seal-Ring and CPAP Mask Kit (medium), Part #73510-669, before applicants' filing date.

Mask 4 Photographs, Respironics Inc., Monarch Mini Mask with Pressure Port, Part #572004, Monarch Headgear, Part #572011, before applicants' filing date.

Mask 5 Photographs, Healthdyne Technologies, Nasal CPAP Mask (medium narrow), Part #702510, before applicants' filing date.

Mask 6 Photographs, Healthdyne Technologies, Soft Series Nasal CPAP Mask, Part #702020, before applicants' filing date.

Mask 7 Photographs, DeVilbiss Healthcare Inc., Small Mask and Seal Rings, Part #73510-668, before applicants' filing date.

Mask 8 Photographs, Respironics Inc., Reusable Contour Mask (medium), Part #302180, before applicants' filing date.

Mask 9 Photographs, Healthdyne Technologies, Healthdyne Large Headgear, before applicants' filing date.

Mask 10 Photographs, Respironics Inc., Soft Cap (medium), Part #302142, before applicants' filing date.

Mask 11 Photographs, Weinmann: Hamburg, Nasalmaskensystem mit Schalldampfer (medium), Part #WN 23105, before applicants' filing date.

Mask 12 Photographs, Lite Care, before applicants' filing date.

Mask 13 Photographs, Healthdyne Technologies, before applicants' filing date.
Mark 14 Photographs, King System, before applicants' filing date.
Mask 15 Photographs, Respironics Inc., Pediatric Mask, before applicants' filing date.
Mask 16 Photographs, Hans Rudolph Inc., Hans Rudolph Silicone Rubber Face Mask/8900, before applicants' filing date.
McPherson et al., "Respiratory Therapy Equipment," Chapter 8. Third Edition, Introduction to Ventilators, pp. 230-253, 1985.
Merriam-Webster Online Dictionary definition of moveable from the 14th century, before applicants' filing date.
New Zealand Appln. No. 2003275762—Examiner's Report No. 3, dated Nov. 18, 2009.
New Zealand Appln. No. 539836—Examination Report, dated Aug. 25, 2005.
New Zealand Appln. No. 564877—Examination Report, dated Dec. 2, 2009.
New Zealand Appln. No. 567375—Examination Report, dated Nov. 17, 2009.
New Zealand Appln. No. 587344—Examination Report, dated Jan. 19, 2012.
New Zealand Appln. No. 587344—Examination Report, dated Aug. 3, 2012.
New Zealand Appln. No. 587820—Examination Report, dated Sep. 13, 2010.
New Zealand Appln. No. 597552—Examination Report. dated Jan. 19, 2012.
New Zealand Appln. No. 597689—Examination Report, dated Jan. 25, 2012.
PCT/AU2003/001163—International Search Report, dated Nov. 4, 2003.
PCT/AU2003/001471—International Search Report, dated Feb. 12, 2004.
PCT/AU2004/000563—International Search Report, dated Jun. 23, 2004.
PCT/AU2004/001760—International Preliminary Report on Patentability, dated Jul. 3, 2006.
PCT/AU2004/001760—International Search Report, dated Jan. 12, 2005.
PCT/AU2004/001813—International Preliminary Report on Patentability, dated Jul. 3, 2006.
PCT/AU2004/001813—International Search Report, dated Mar. 7, 2005.
PCT/AU2004/001832—International Preliminary Report on Patentability, dated Jul. 3, 2006.
PCT/AU2004/001832—International Search Report, dated Mar. 24, 2005.
PCT/AU2005/000803—International Search Report, dated Jun. 30. 2005.
PCT/AU2005/000850—International Preliminary Report on Patentability, dated Dec. 20, 2006.
PCT/AU2005/000850—International Search Report, dated Aug. 12. 2005.
PCT/AU2006/000032—International Preliminary Report on Patentability, dated Jul. 17, 2007.
PCT/AU2006/000032—International Search Report, dated May 15, 2006.
PCT/AU2006/000770—International Search Report, dated Aug. 3, 2006.
PCT/AU2006/001570—International Search Report, dated Jan. 5, 2007.
PCT/AU2007/001051—International Search Report, dated Nov. 5, 2007.
PCT/AU2007/001052—International Search Report, dated Oct. 9, 2007.
PCT/AU2007/001456—International Search Report, dated Dec. 12, 2007.
PCT/AU2007/001936—International Search Report, dated Mar. 4, 2008.
PCT/AU2009/000240—International Search Report, dated May 21, 2009.
PCT/AU2009/000262—International Search Report, dated Jun. 9, 2009.
PCT/AU2009/001102—International Search Report, dated Dec. 11, 2009.
PCT/AU2009/001144—International Search Report, dated Dec. 8, 2009.
PCT/AU2010/000657—International Search Report, dated Sep. 9, 2010.
Product Brochure for ResMed "Sullivan® Mirage™—The Mirage is Real. A Perfect Fit-First Time," © 1997 ResMed Limited, 4 pages.
Product Brochure for ResMed "Sullivan® Mirage™—The Mirage is Real. A Perfect Fit-First Time," © 1998 ResMed Limited, 4 pages.
ResMed Co.—Mask Products—http://resmed.com/portal/site/ResMedUS/index.jsp?, before applicants' filing date.
ResMed Ltd., "Improving patient compliance with the ResMed Range of Mask Systems The Ultimate Interface for CPAP treatment," before applicants' filing date, 4 pages.
Respironics Co.—Mask Family—http://masksfamily.respironics.com/, before Applicant's filing date.
Snapp Nasal Interface, Tiara Medical Systems, Inc.—http://tiaramed.com/asp_shops/shopdisplayproducts.asp?id=109&cat=SNAPP%2A+Nasal+Interface, before applicants' filing date.
"Somnomask" brochure, 1999 along with various invoices relating to the "Somnomask".
Somnotron CPAP—Great WM 2300 Instruction Manual, Weinmann Hamburg, 1991, 11 pages.
Subbu Venkatraman et al., "Review Skin Adhesives and Skin Adhesion I. Transdermal Drug Delivery Systems," Biomaterials, vol. 19, 1998, pp. 1119-1136.
The ResMed Range of Mask Systems, product brochure, Nov. 1995, 4 pages.
Unsolicited email from Elson Silva, PhD, dated Mar. 28, 2008, "Requesting IDS of US 6,766,817 for patents on fluids moving on porosity by Unsaturated Hydraulic Flow," (email provided in both HTML and plain text format).
Photo of Weinmann Mask (manufactured 1991).
U.S. Appl. No. 12/083,779—Office Action including PTO-892 listings, dated Feb. 7, 2012.
U.S. Appl. No. 12/083,779—Office Action including PTO-892 listings, dated Sep. 28, 2012.
U.S. Appl. No. 60/424,686, filed Nov. 8, 2002 (expired).
U.S. Appl. No. 60/483,622, filed Jul. 1, 2003 (expired).
U.S. Appl. No. 60/533,214, filed Dec. 31, 2003 (expired).
U.S. Appl. No. 60/634,802, filed Dec. 10, 2004 (expired).
U.S. Appl. No. 60/643,121, filed Jan. 12, 2005 (expired).
U.S. Appl. No. 60/645,672, filed Jan. 21, 2005 (expired).
U.S. Appl. No. 60/795,615, filed Apr. 28, 2006 (expired).
U.S. Appl. No. 60/833,841, filed Jul. 28, 2006 (expired).
U.S. Appl. No. 60/835,442, filed Aug. 4, 2006 (expired).
U.S. Appl. No. 60/852,649, filed Oct. 19, 2006 (expired).
U.S. Appl. No. 60/874,968, filed Dec. 15, 2006 (expired).
U.S. Appl. No. 60/907,856, filed Apr. 19, 2007 (expired).
U.S. Appl. No. 60/924,241, filed May 4, 2007 (expired).
U.S. Appl. No. 60/929,393, filed Jun. 25, 2007 (expired).
U.S. Appl. No. 60/935,179, filed Jul. 30, 2007 (expired).
U.S. Appl. No. 60/935,336, filed Aug. 8, 2007 (expired).
U.S. Appl. No. 60/996,160, filed Nov. 5, 2007 (expired).
U.S. Appl. No. 61/006,409, filed Jan. 11, 2008 (expired).
U.S. Appl. No. 61/064,818, filed Mar. 28, 2008 (expired).
U.S. Appl. No. 61/071,512, filed May 2, 2008 (expired).
U.S. Appl. No. 61/213,326, filed May 29, 2009 (expired).
U.S. Appl. No. 61/222,711, filed Jul. 2, 2009 (expired).
U.S. Appl. No. 61/263,175, filed Nov. 20, 2009 (expired).
U.S. Appl. No. 61/272,162, filed Aug. 25, 2009 (expired).
U.S. Appl. No. 61/272,250, filed Sep. 4, 2009 (expired).
U.S. Appl. No. 12/230,120, filed Aug. 8, 2008 (corresponds to JP 2009-0050156, Feb. 2009).
Webster's New World Dictionary, Third College Edition 1988, definition for engaged and flexible, before applicants' filing date.
Webster's Third New International Dictionary, 1993, Dictionary definition for adjustable, bendable, and mild steel, before applicants' filing date.

U.S. Appl. No. 13/834,189, filed Mar. 2013, Hitchcock et al.
U.S. Appl. No. 13/870,678, filed Apr. 2013, Kwok et al.
Notice of Reasons for Rejection and English Translation for corresponding JP Application No. 2010-548986, dated Apr. 16, 2003, 5 pages.
First Examination Report for corresponding NZ Application No. 607032, dated Feb. 18, 2013, 2 pages.
Patent Examination Report No. 1 for corresponding AU Application No. 2009221630, dated Mar. 21, 2013, 3 pages.

Office Action issued Apr. 10, 2013 in U.S. Appl. No. 13/745,077, including PTO-892.
Office Action issued Apr. 8, 2013 in U.S. Appl. No. 13/747,701, including PTO-892.
Notice of Allowance issued Mar. 28, 2013 in U.S. Appl. No. 12/736,024.

* cited by examiner

MASK SYSTEM

CROSS-SECTION TO RELATED APPLICATIONS

This application is a continuation application of application Ser. No. 12/736,024, filed Sep. 2, 2010, which is the U.S. national phase of International Application No. PCT/AU2009/000241, filed Feb. 27, 2009, which designated the U.S. and claims the benefit of U.S. Provisional Application Nos. 61/064,406, filed Mar. 4, 2008, 61/071,893, filed May 23, 2008, and 61/136,617, filed Sep. 19, 2008, each of which is incorporated herein by reference in its entirety.

FIELD OF THE INVENTION

The present invention relates to a mask system used for treatment, e.g., of Sleep Disordered Breathing (SDB) with Continuous Positive Airway Pressure (CPAP) or Non-Invasive Positive Pressure Ventilation (NIPPY).

BACKGROUND OF THE INVENTION

Patient interfaces, such as a full-face or nasal mask systems, for use with blowers and flow generators in the treatment of sleep disordered breathing (SDB), typically include a soft face-contacting portion, such as a cushion, and a rigid or semi-rigid shell or frame module. In use, the interface is held in a sealing position by headgear so as to enable a supply of air at positive pressure (e.g., 2-30 cm $H_2O$) to be delivered to the patient's airways.

One factor in the efficacy of therapy and compliance of patients with therapy is the comfort and fit of the patient interface.

The present invention provides alternative arrangements of mask systems to enhance the efficacy of therapy and compliance of patients with therapy.

SUMMARY OF THE INVENTION

One aspect of the invention relates to a mask system including a frame module and a cushion module provided to the frame module. The cushion module includes a main body defining a breathing chamber and a cushion adapted to form a seal with the patient's face. The frame module and the cushion module are co-molded with one another. The cushion module is constructed of a first, relatively soft, elastomeric material and the frame module is constructed of a second material that is more rigid than the cushion module. At least a portion of the cushion module includes a concertina section having a plurality of folds. Each of the folds has a side wall with the side walls of the folds becoming progressively longer away from the patient's face.

Another aspect of the invention relates to a cushion module including a main body defining a breathing chamber and a cushion adapted to form a seal with the patient's face. The main body and the cushion are co-molded with one another. The cushion is constructed of a first, relatively soft, elastomeric material and the main body is constructed of a second material that is more rigid than the cushion. At least a portion of the main body includes a concertina section.

Another aspect of the invention relates to a method for constructing a cushion module including molding a first part of the cushion module with a first, relatively soft, elastomeric material, co-molding a second part of the cushion module to the first part with a second material that is more rigid than the first material, and molding at least a portion of the second part to include a concertina section.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIGS. 5-1 is a rear view of a cushion according to an embodiment of the present invention;

FIG. 5-2 is a front view of the cushion shown in FIG. 5-1 with a partial cut-away;

FIG. 5-3 is a cross-section view through line 5-3-5-3 in FIG. 5-1;

FIG. 5-4 is a cross-section view through line 5-4-5-4 in FIG. 5-1;

FIG. 5-5 is a cross-section view through line 5-5-5-5 in FIG. 5-1;

FIGS. 6-1 to 6-3 illustrate top, front, and side views respectively of a concertina section according to an embodiment of the present invention;

DETAILED DESCRIPTION OF ILLUSTRATED EMBODIMENTS

Figure 1:
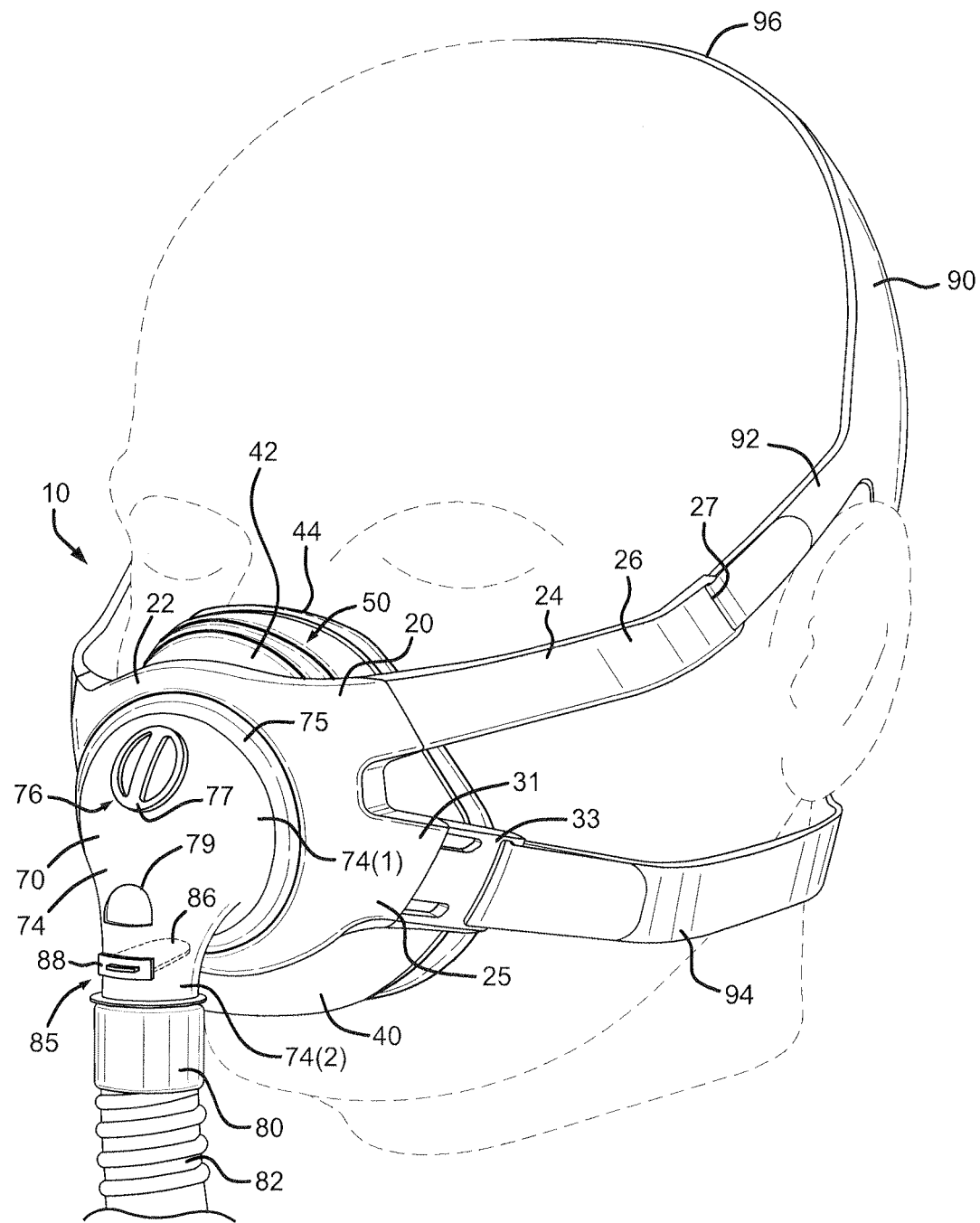
FIG. 1 is a front perspective view of a mask system according to an embodiment of the present invention.

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

While each embodiment below is described as including a full-face interface type, each embodiment may be adapted for use with other suitable interface types. That is, the interface type is merely exemplary, and each embodiment may be adapted to include other interface types, e.g., nasal interface, etc.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen.

1. Mask System

FIGS. 1-4 illustrate a mask system 10 according to an embodiment of the present invention. In this embodiment, the mask system 10 includes a full-face or oro-nasal interface. The mask system 10 includes a frame module 20, a cushion module 40 provided to the frame module 20 and adapted to form a seal with the patient's face, and an elbow module 70 provided to the frame module 20 and adapted to be connected to an air delivery tube that delivers breathable gas to the patient. Headgear 90 may be removably attached to the frame module 20 to maintain the mask system 10 in a desired adjusted position on the patient's face. The mask system is intended for use in positive pressure therapy for users with obstructive sleep apnea (OSA) or another respiratory disorder.

As described below, the mask system 10 provides a modular design that allows different styles and/or sizes of the frame module 20, cushion module 40, and elbow module 70 to be interchanged or mixed and matched with one another to provide a more customized mask system for the patient. In addition, such design allows selected modules to be easily replaced, e.g., treatment requirements change, worn out or damaged, etc.

1.1 Frame Module

The frame module 20 (e.g., constructed from polycarbonate, polypropylene, thermoplastic elastomer (TPE), Pocan®, etc.) is structured to maintain the cushion module 40 and the elbow module 70 in an operative position with respect to the patient's face. In addition, the frame module 20 is structured to removably attach to the headgear 90 adapted to maintain the mask system 10 in a desired position on the patient's face.

Figure 2:
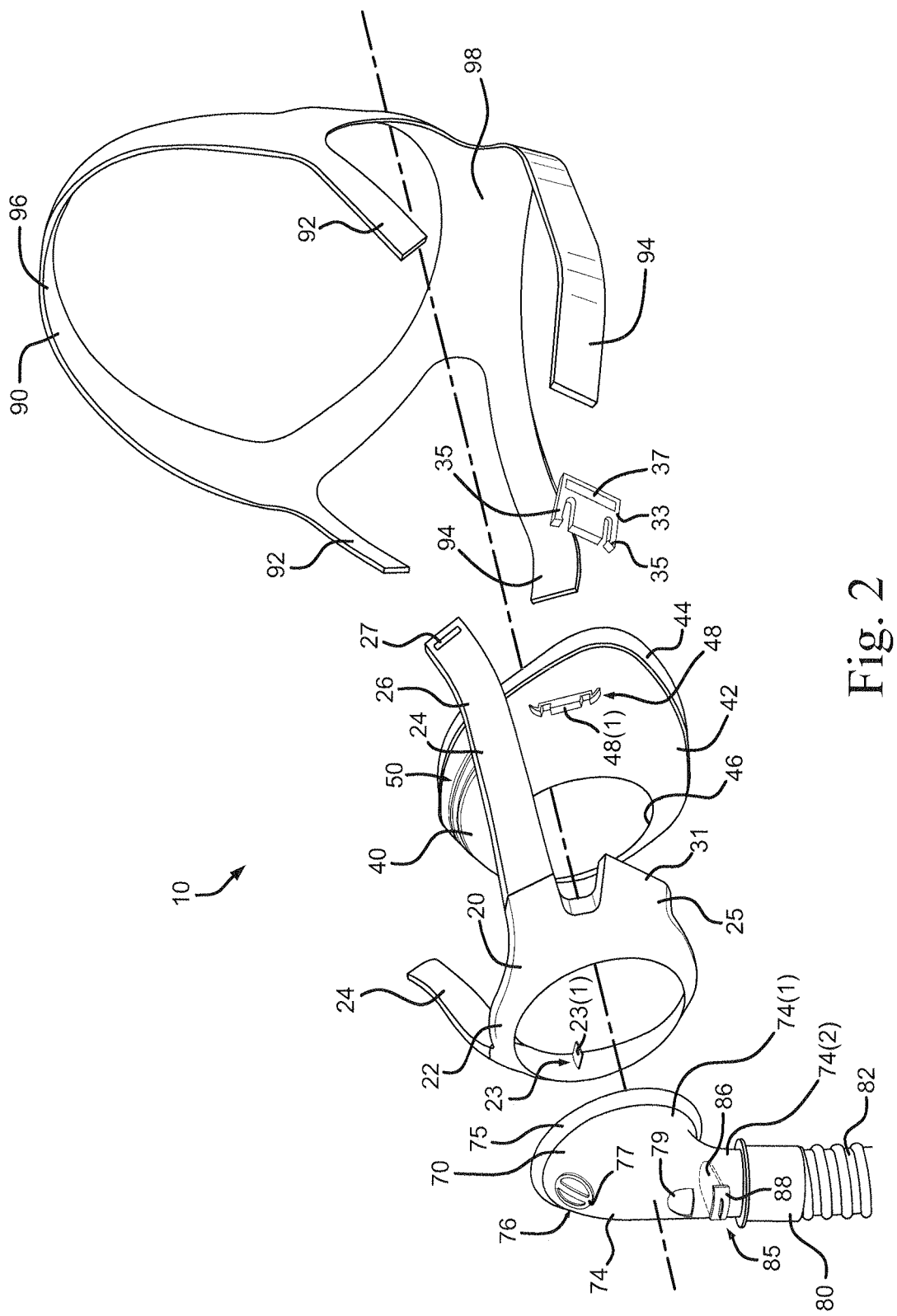
FIG. 2 is an exploded view of the mask system shown in FIG. 1.

As best shown in FIG. 2, the frame module 20 (also referred to as a skeleton frame) includes an open construction that provides an annular or part annular retaining portion 22 structured to retain the cushion module 40 and the elbow module 70. The frame module 20 also includes upper and lower headgear connectors 24, 25 on each side of the retaining portion 22.

In the illustrated embodiment, each upper headgear connector 24 includes an elongated arm 26 and a slot 27 at the free end of the arm 26 adapted to receive a respective headgear strap in use. Each arm 26 may be at least semi-rigid (i.e., rigidizer) to stabilize the mask system on the patient's face. Also, each arm 26 is suitably formed, shaped, or contoured to follow the contours of the patient's face and avoid line of sight in use. A cheek pad may be provided to the inner surface of the arm 26 to support the arm 26 on the patient's cheek in use.

Each lower headgear connector 25 includes a clip receptacle 31 adapted to be removably interlocked with a headgear clip 33 associated with a respective headgear strap. As best shown in FIG. 2, each clip 33 includes two spring arms 35 adapted to interlock with the respective clip receptacle 31 with a snap-fit and a slot 37 adapted to receive a respective headgear strap in use.

In an embodiment, the arm 26 may be removably coupled to the frame module 20, e.g., arm 26 includes clip structure adapted to removably interlock with a clip receptacle provided to the frame module 20. This arrangement allows different styles of upper and lower headgear connectors to be used with the frame module, e.g., arms for both upper and lower headgear connectors, clips for both upper and lower headgear connectors, different length arms for upper and lower headgear connectors, etc.

However, the frame module 20 may provide other suitable arrangements for attaching headgear straps of headgear. Also, the frame module 20 may include one or more additional components, e.g., forehead support.

The mask system 10 is provided without a forehead support adapted to engage the patient's forehead. This provides the mask system 10 with a less obtrusive arrangement which does not significantly affect the patient's field of view.

1.2 Cushion Module

The cushion module 40 is structured to interface with the frame module 20 and form a seal with patient's nose and mouth in use.

The cushion module 40 includes a main body 42 and a cushion 44 provided to the main body 42. In use, the main body 42 defines a breathing chamber and is adapted to interface with or otherwise attach to the frame module 20 and the cushion 44 provides a sealing portion or sealing ring adapted to form a seal with the patient's nose and/or mouth. Also, the main body 42 includes an opening 46 that is adapted to communicate with the elbow module 70.

In the illustrated embodiment, the cushion 44 is a full-face cushion adapted to engage the patient's face generally along nasal bridge, cheek, and lower lip/chin regions of the patient's face. However, other cushion interfaces are possible, e.g., nasal.

Figures 1, 5:
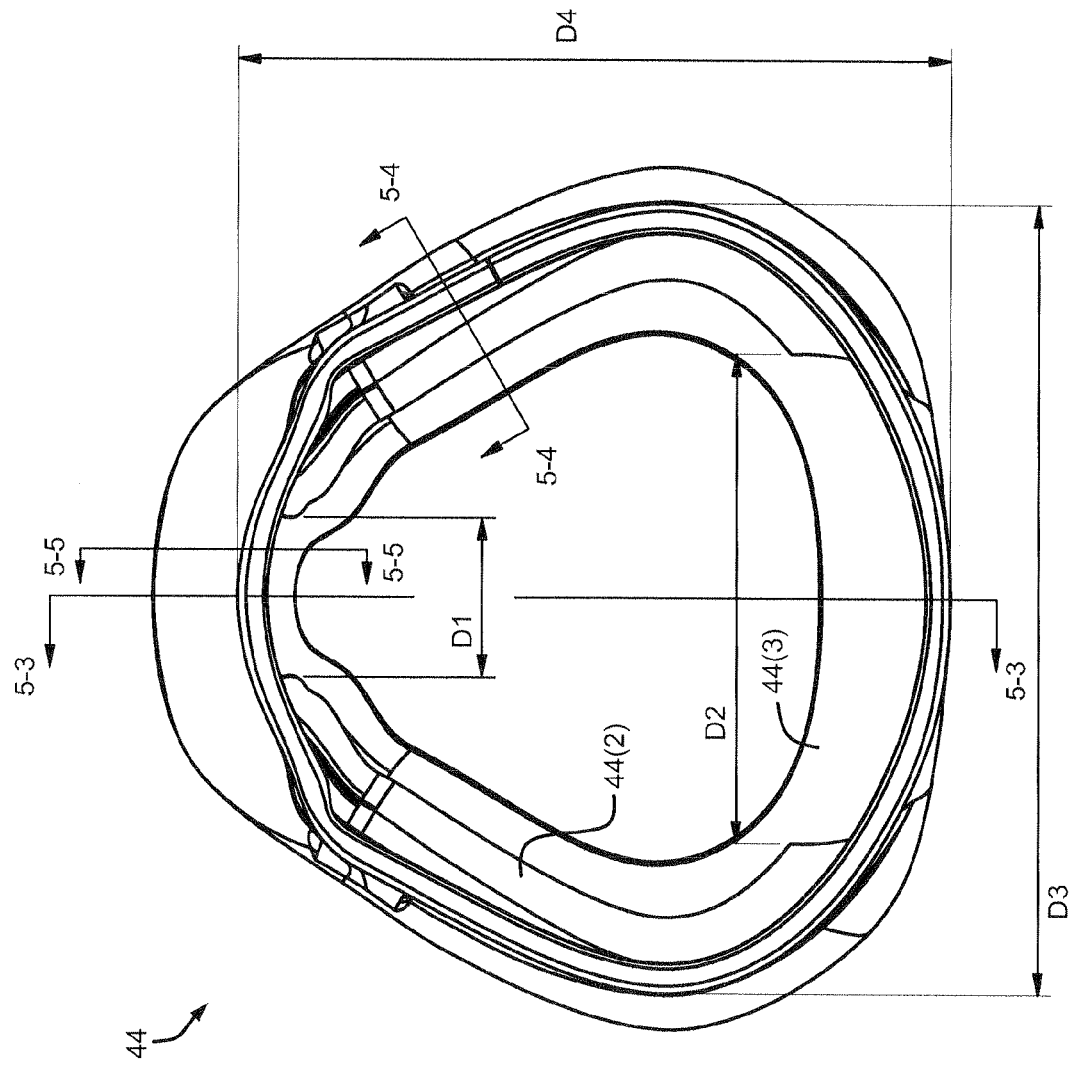
Figures 2, 5:
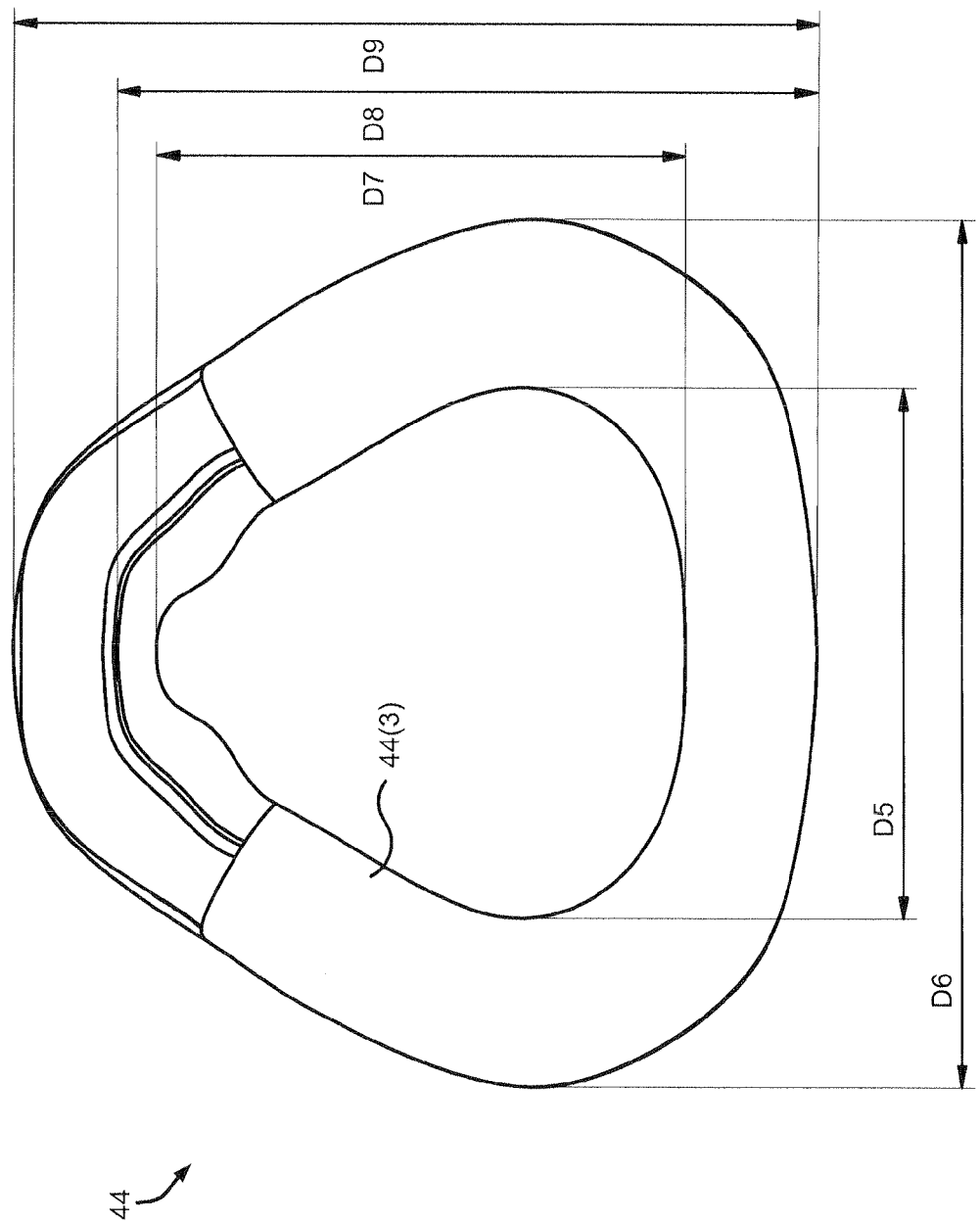
Figures 3, 5:
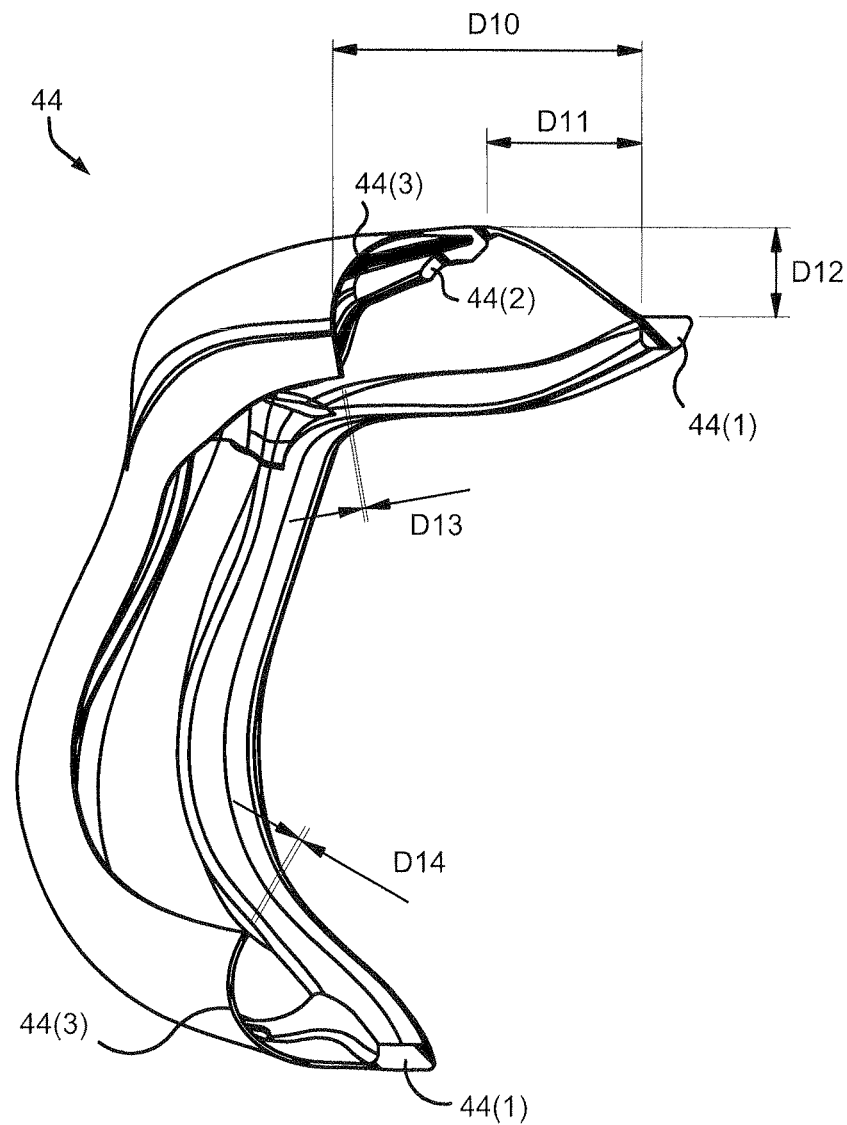
Figure 5:
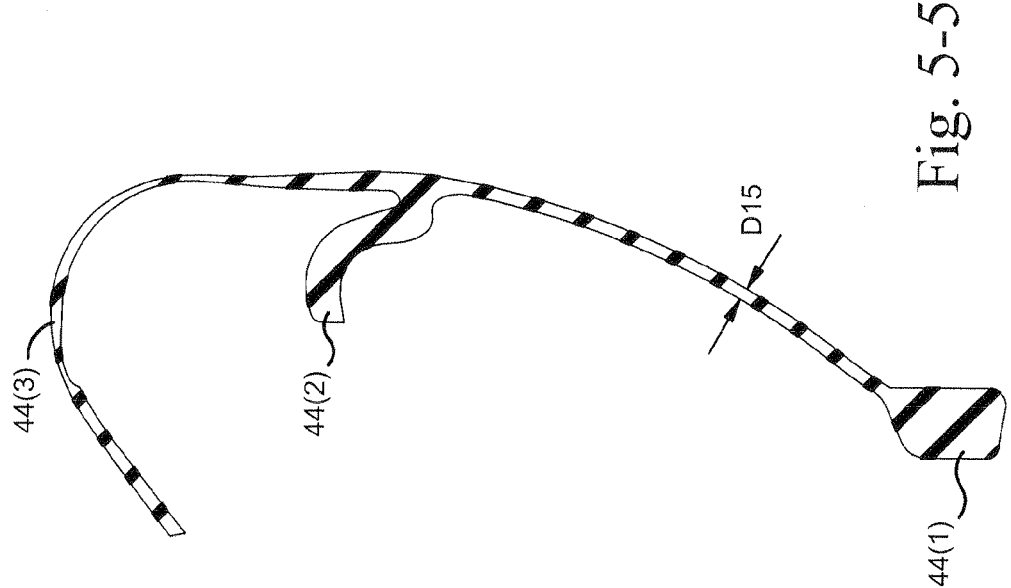
Figures 4, 5:
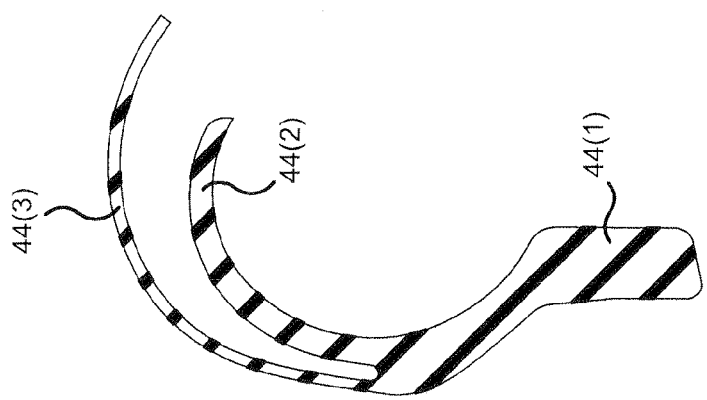

FIGS. 5-1 to 5-5 illustrate various views of a cushion (e.g., constructed of silicone) according to an embodiment of the present invention. As illustrated, the cushion 44 includes a base wall 44(1) provided to the main body 42, an undercushion layer (UCL) 44(2) extending away from the base wall 44(1), and a membrane 44(3) provided to substantially cover the UCL 44(2) and provide a sealing structure. In the illustrated embodiment, the cushion 44 is structured to sit lower on the nasal bridge to reduce mask obtrusiveness and improve "line of sight" in use.

Figure 3:
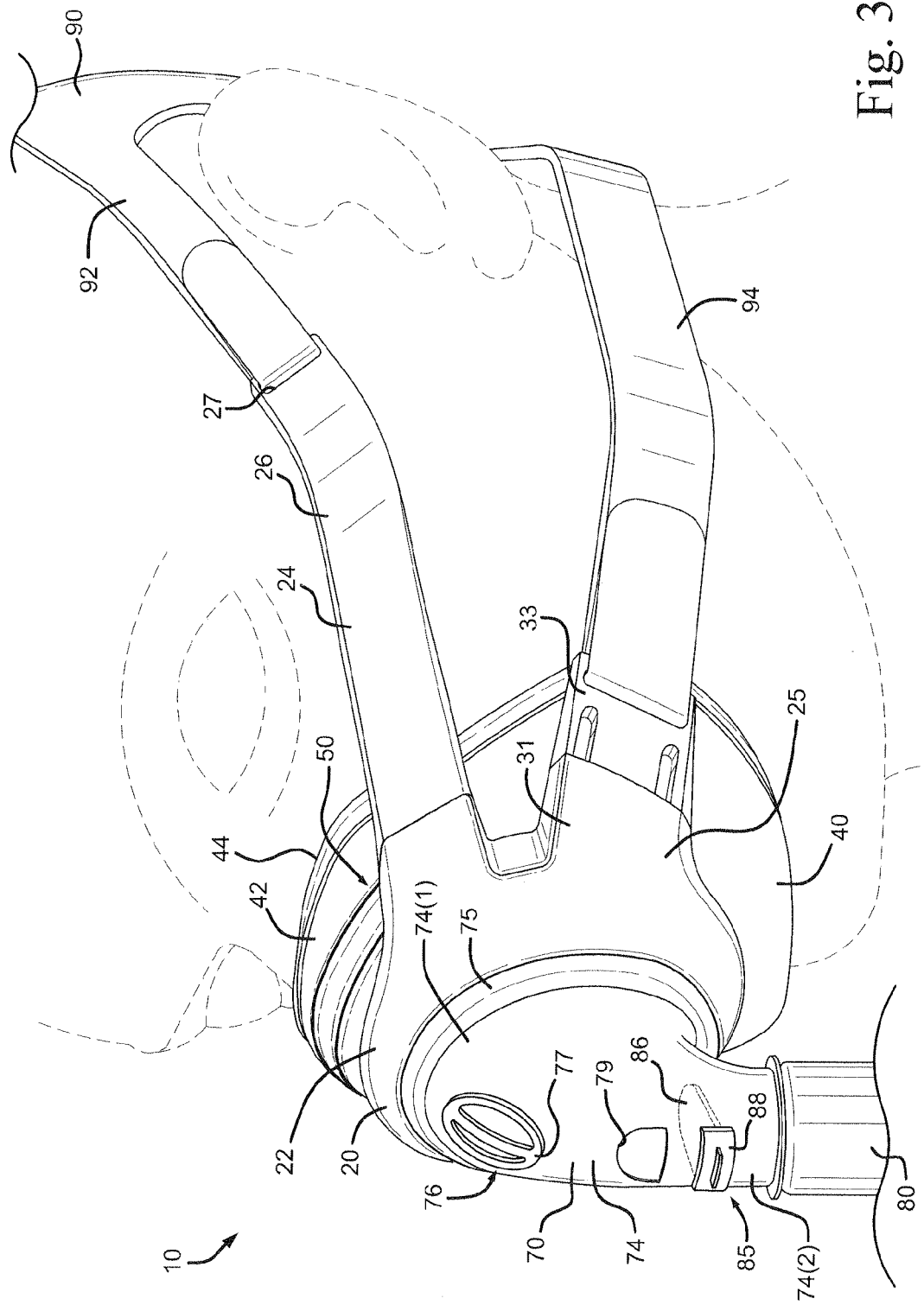
FIG. 3 is an enlarged front perspective view of the mask system shown in FIG. 1.

Also, as best shown in FIGS. 5-3 and 5-5, the UCL 44(2) design in the nasal bridge region is structured to provide improved stability across the nasal bridge in use. As shown in FIGS. 5-1 and 5-3, the UCL is not provided in the lower lip/chin region. However, other arrangements of the UCL are possible, e.g., UCL around entire perimeter.

In an embodiment of the cushion shown in FIGS. 5-1 to 5-5, D1 may be about 15-20 mm, e.g., 18.2 mm, D2 may be about 53-59 mm, e.g., 55.8 mm, D3 may be about 88-93 mm, e.g., 90 mm, D4 may be about 78-83 mm, e.g., 81.1, D5 may be about 58-63 mm, e.g., 60 mm, D6 may be about 95-100 mm, e.g., 98.1 mm, D7 may be about 57-62 mm, e.g., 59.7 mm, D8 may be about 77-82 mm, e.g., 79 mm, D9 may be about 88-93 mm, e.g., 90.7 mm, D10 may be about 30-35 mm, e.g., 33.1 mm, D11 may be about 14-19 mm, e.g., 16.4 mm, D12 may be about 8-13 mm, e.g., 9.6 mm, D13 may be about 0.3-0.5 mm, e.g., 0.35 mm, D14 may be about 0.4-0.6 mm, e.g., 0.5 mm, and D15 may be about 0.3-0.5 mm, e.g., 0.4 mm. Although specific dimensions and ranges are indicated, it is to be understood that these dimensions and ranges are merely exemplary and other dimensions and ranges are possible depending on application. For example, the exemplary dimensions may vary by 10-20% or more or less depending on application.

The mask system 10 may be provided with a number of different cushion modules 40, e.g., each having cushions of different styles and/or sizes (e.g., depending on patient preference and/or fit). For example, the main body 42 of each cushion module may include a common or universal configuration for interfacing with the frame module 20, and the cushion 44 may include different styles and/or sizes. This provides a modular arrangement that allows the frame module 20 to be selectively (e.g., and removably) coupled to one of multiple cushion modules. For example, the different cushion modules may include different size cushions (e.g., small, medium, and large) and may include a different cushion structures.

Similarly, the cushion module 40 may be provided with different frame modules 20, e.g., each frame module having a different style and/or size (e.g., frame module with forehead support, frame module with different arrangement/style of headgear connectors, etc).

1.2.1 Co-Molding Main Body and Cushion

In an embodiment, as shown in FIGS. 1-4, the main body 42 and cushion 44 may be co-molded with one another to form a one-piece, integrated component. For example, the main body 42 may be molded of a first material adapted to interface with the frame module 20 and the cushion 44 may be co-molded onto the main body 42 of a second material adapted to interface with patient's face.

In such embodiment, the cushion 44 may be constructed of a relatively soft elastomeric material (e.g., silicone) for sealing and the main body 42 may be constructed of a more rigid material than the cushion 44 (e.g., polycarbonate, polypropylene) for interfacing with the frame.

Co-molding the main body 42 to the cushion 42 provides a chemical bond without necessarily forming a mechanical interlock. As a result, the connection includes no cracks, a gas tight seal, and clean interface. Moreover, such co-molded connection relaxes tolerances as the mold materials are sufficiently flexible to fill in any gaps at the interface between the main body 42 and the cushion 44. Also, the co-molded cushion module 40 provides a reduced part count (reduced cost) and facilitates assembly/disassembly to the frame module 20.

The frame module 20 is structured to hold and secure the cushion module 40 in an operative position with respect to the patient's face. As shown in FIG. 2, the annular retaining portion 22 includes an interfacing structure 23 along an inner edge that is adapted to interface with or otherwise removably connect to an interfacing structure 48 along the outer perimeter of the main body 42 of the cushion module 40 (e.g., see FIG. 2). In the illustrated embodiment, the interfacing structure 23 is in the form of opposed flanges 23(1) that are adapted to interlock with respective locking structures 48(1) provided on opposing sides of the main body 42. However, other suitable arrangements for attaching the cushion module 40 to the frame module 20 are possible, e.g., friction fit, snap-fit, mechanical interlock, or other suitable attachment mechanism.

For example, the cushion module 40 may be coupled to the frame module 20 in a manner that allows the cushion module 40 to be locked in different angular positions with respect to the frame module 20, e.g., pivotally mounted.

1.2.2 Co-Molding Cushion Module and Frame

Figure 7:
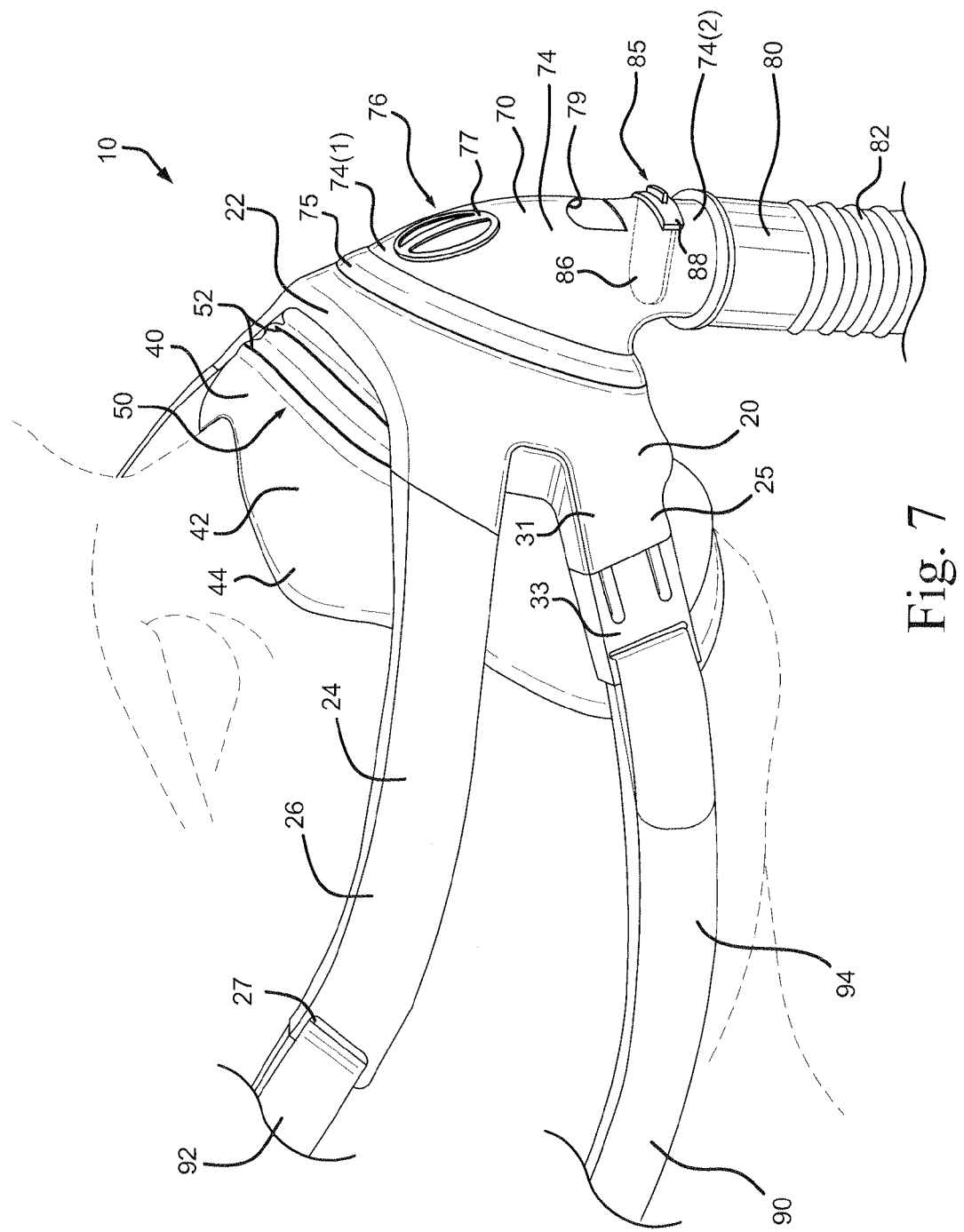
FIG. 7 is a side view of a mask system including a cushion module according to a variation of the present invention.

In the arrangement shown in FIG. 7, the main body 42 and cushion 44 may be integrally formed in one piece, e.g., of a silicone material. That is, the cushion module 40 may have the same shape and structure as described above, but be integrally molded of the same material, e.g., silicone.

In an embodiment, the integrally formed cushion module 40 may be co-molded to the frame module 20, e.g., constructed of polycarbonate or polypropylene. For example, frame module 20 may be constructed of a relatively rigid material (e.g., polycarbonate or polypropylene) and the cushion module 40 may be co-molded onto the frame module 20 of a relatively soft elastomeric material (e.g., silicone).

1.2.3 Concertina Section

Figure 4:
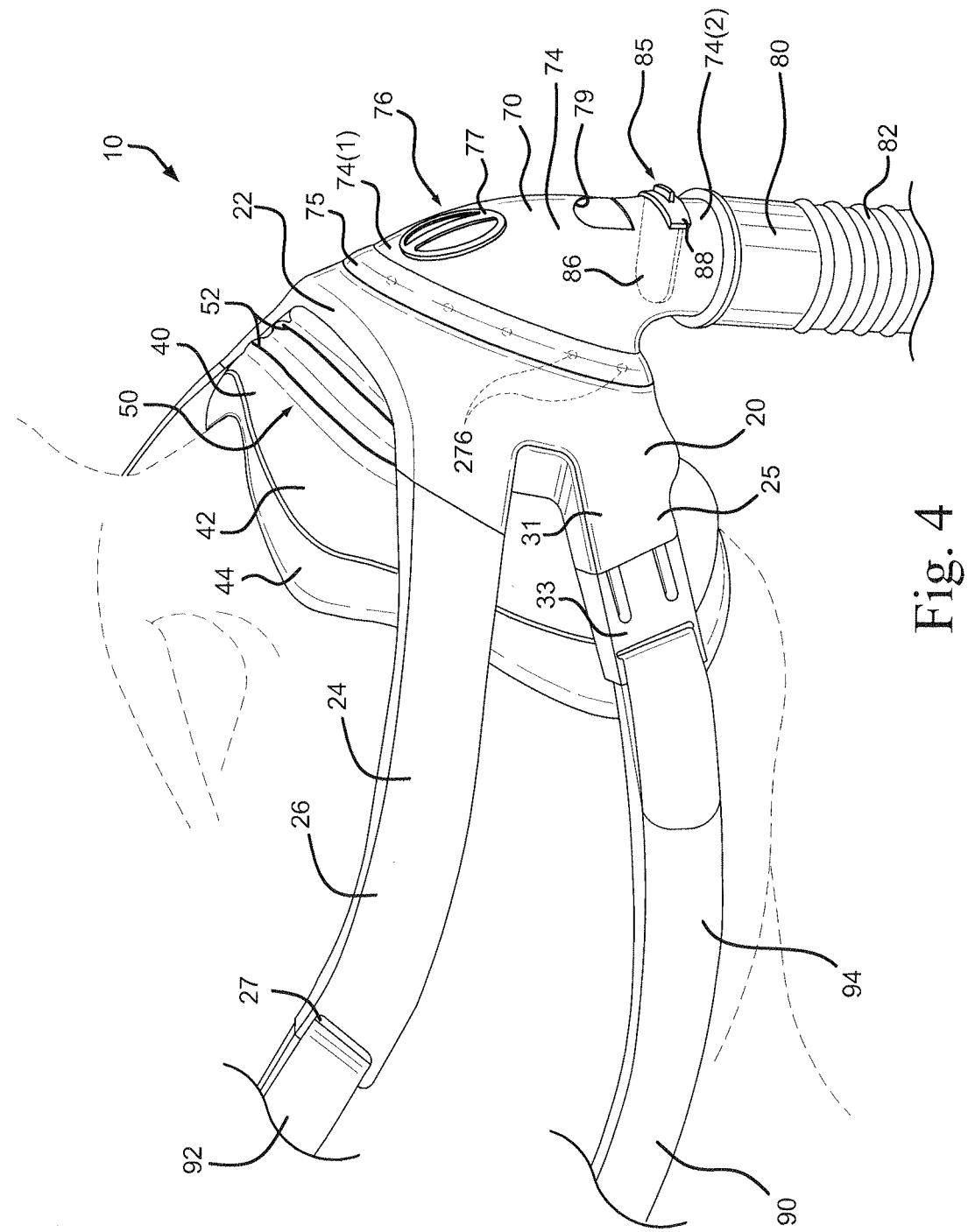
FIG. 4 is a side view of the mask system shown in FIG. 1.

As best shown in FIGS. 4 and 7, a concertina section 50 is provided in a nasal bridge region of the cushion module 40. As illustrated, the concertina section 50 includes a bellows structure with one or more folds 52 that provide a higher degree of flexibility or increased movement to the main body 42. That is, the concertina section 50 provides a higher level of adaptability or flexibility to the nasal bridge region of the cushion module 40 which is a more sensitive region of the patient's face in use. Moreover, the concertina section 50 provides increased movement without compromising seal.

Figures 1, 6:
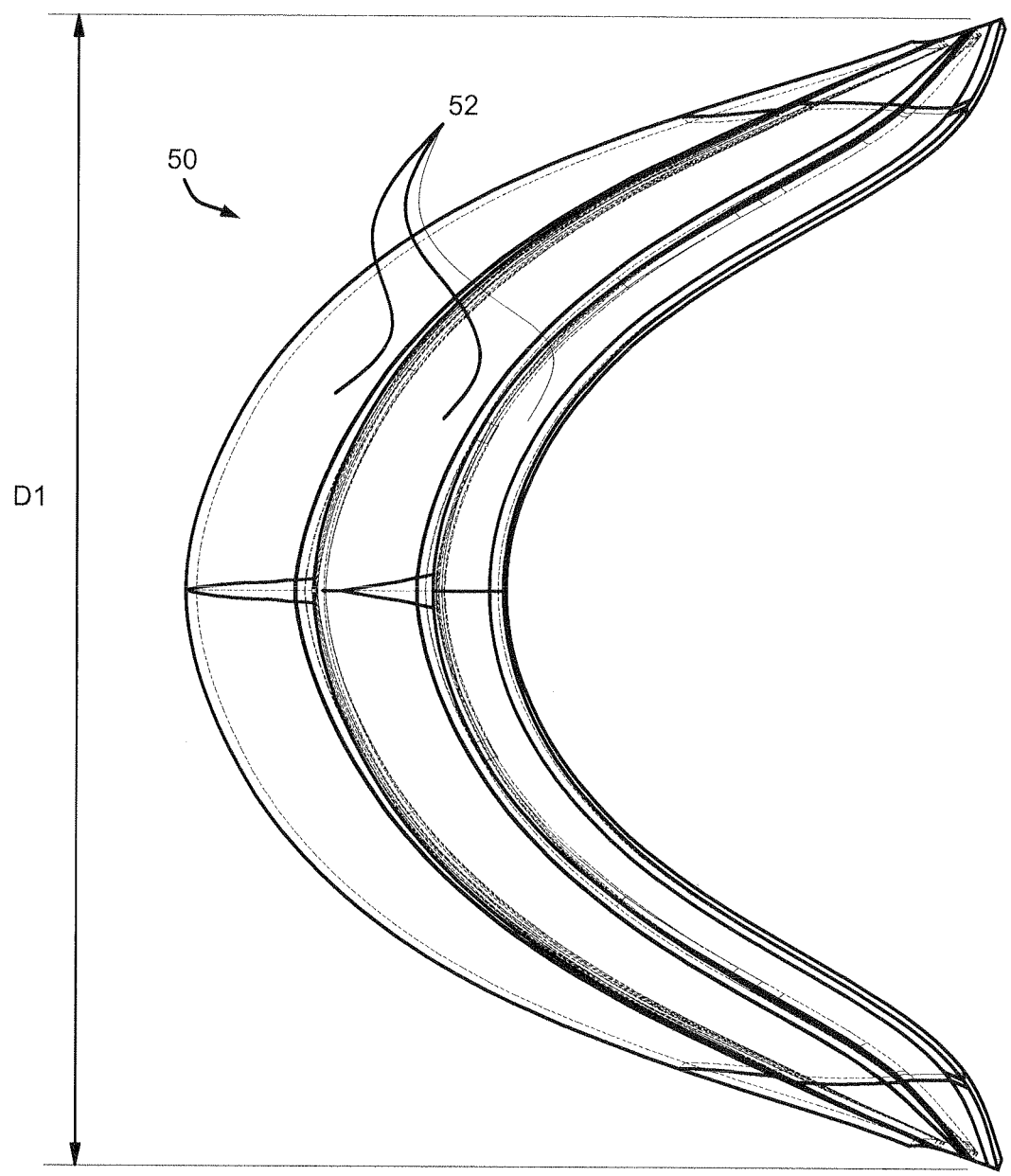
Figures 2, 6:
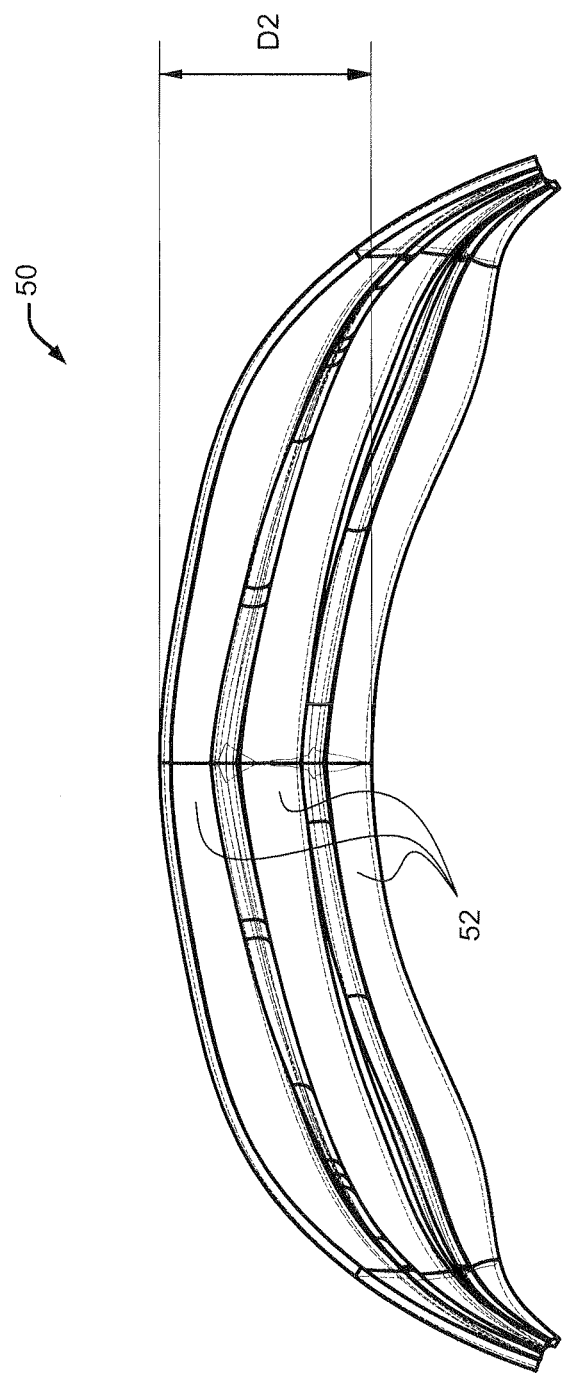
Figures 3, 6:
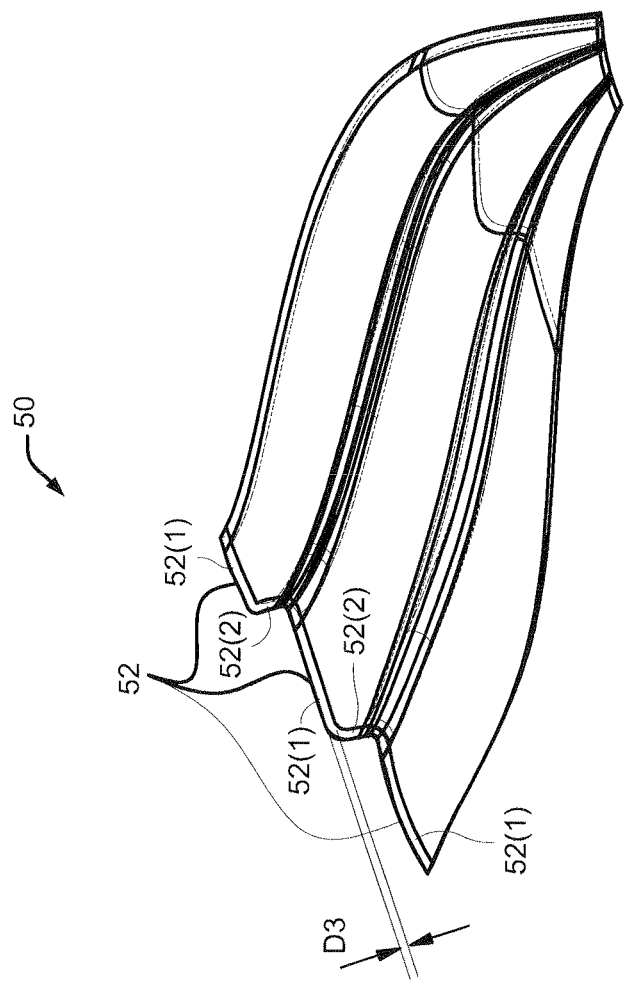

FIGS. 6-1 to 6-3 illustrate various views of a concertina section 50 (isolated from the remainder of the cushion module) with one or more folds 52 according to an embodiment of the present invention. As best shown in FIG. 6-3, the folds may have different lengths, depths, and/or contours with respect to one another to optimize the concertina effect, e.g., provide sufficient degree of movement without compromising seal. For example, as shown in FIG. 6-3, each fold 52 includes a first side wall 52(1) and a second side wall 52(2) that interconnects adjacent side walls 52(1).

In the illustrated embodiment, the first side walls 52(1) and/or the second side walls 52(2) may become progressively longer away from the patient's face. For example, the first side wall 52(1) and/or the second side wall 52(2) adjacent patient's face, or the combination of side walls 52(1) and 52(2), may have a length that is longer than and in some cases significantly longer than the adjacent side wall 52(1) and/or 52(2) (e.g., one side wall at least 25% greater than and up to 5× as long as the other side wall, e.g., 1×, 2×, 3×, or 4×).

The folds may be constructed and arranged to provide a predetermined order of movement or folding, e.g., folds structured to fold in a sequential or progressive manner wherein one fold collapses before an adjacent fold collapses. For example, upon application of force, the folds closest to the patient's face may fold or collapse before the folds furthest from the patient's face. Also, the folds may be constructed and arranged to provide various degrees of fold or collapse, e.g., folds may fold or collapse more than others.

In an embodiment of the concertina section shown in FIGS. 6-1 to 6-3, D1 may be about 50-60 mm, e.g., 55.7 mm, D2 may be about 5-15 mm, e.g., 9.7 mm, and D3 may be about 0.3-0.5 mm, e.g., 0.4 mm. Although specific dimensions and ranges are indicated, it is to be understood that these dimensions and ranges are merely exemplary and other dimensions and ranges are possible depending on application. For example, the exemplary dimensions may vary by 10-20% or more or less depending on application.

It should be appreciated that a concertina section 50 may be provided in other regions of the cushion module 40, e.g., depending on patient comfort. For example, the concertina section 50 may be provided around the entire perimeter of the cushion module 40 or may be provided in selected regions of the cushion module 40.

Also, the flexibility of the concertina section 50 may be varied and may be varied in different regions of the cushion module 40, e.g., depending on patient comfort. For example, the cushion module 40 may include a concertina section in the nasal bridge region with a relatively high degree of flexibility and a concertina section in the lower lip/chin region with a relatively low degree of flexibility. The flexibility of the concertina section 50 may be varied by varying the number of folds 52 (e.g., 1-5 folds), the wall lengths, the wall thickness of the folds 52, the depth of the folds 52, etc.

As noted above, the cushion module may be co-molded of two parts with different materials/rigidities or may be integrally formed of the same material. In both embodiments, the concertina section may be provided in the main body and/or the cushion.

In FIGS. 1-4, the cushion module 40 is co-molded of two parts (i.e., main body 42 and cushion 44) with the concertina section 50 provided in the main body 42. The main body 42 and cushion 44 include different rigidities in order to optimize the function of each part. For example, one part (i.e., cushion 44) may be constructed of a relatively soft, supple material to optimize the sealing effect and the other part (i.e., main body 42) may be constructed of a more rigid material to provide adequate support for the cushion while at the same time allowing a sufficient degree of movement to optimize the concertina effect. While the main body is more rigid than the cushion, the main body may be constructed of a flexible material to allow the concertina effect.

In FIG. 7, the main body 42 and cushion 44 are integrally formed in one piece with the concertina section 50 provided in the main body 42. The material properties and/or dimensions may be selectively modified to optimize sealing and concertina effects.

Figure 8:
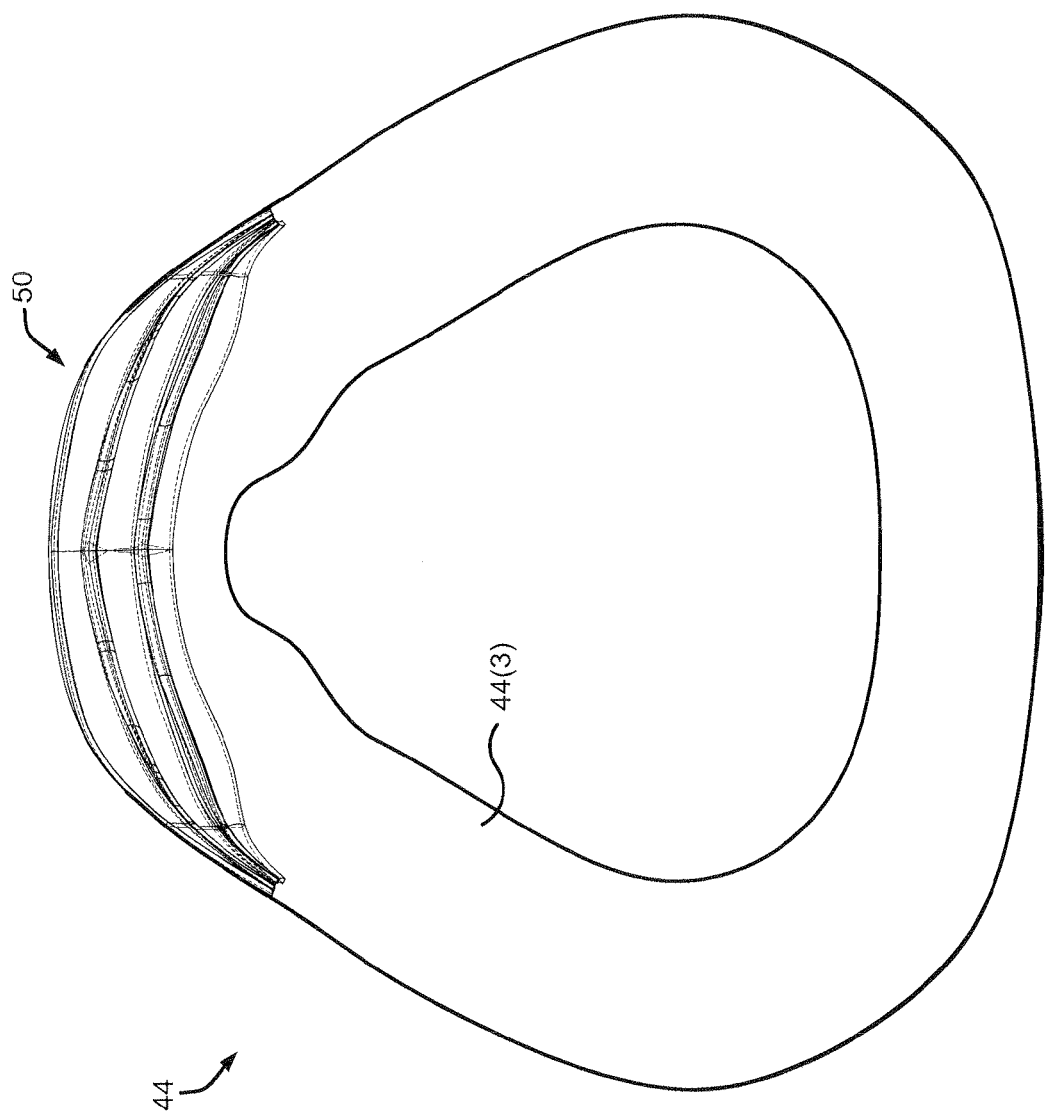
FIG. 8 illustrates a cushion including a concertina section according to an embodiment of the present invention.

For both embodiments of FIGS. 1-4 and 7, it should be appreciated that the concertina section may be alternatively provided in the cushion 44 or in both the main body 42 and cushion 44. For example, FIG. 8 illustrates a concertina section 50 integrally formed with the cushion 44 in the nasal bridge region.

1.3 Elbow Module

The elbow module 70 includes an elbow 74, a vent arrangement 76 provided to the elbow 74 for gas washout, and an anti-asphyxia valve (AAV) 85 provided to the elbow 74.

In an embodiment, the mask system may be provided with a number of different elbow modules 70, e.g., each having a vent arrangement, AAV (in the case of an oro-nasal mask), and/or elbow of different styles and/or sizes. In the illustrated embodiment, the vent arrangement 76 and AAV 85 are structured to be removably attachable to the elbow 74. This provides a modular arrangement that allows the elbow module 70 to be selectively and removably coupled to one of multiple vent arrangements 76 and/or AAVs 85. This also allows the vent arrangement and AAV to be easily replaced, e.g., if damaged.

1.3.1 Elbow

The elbow 74 (e.g., constructed of a relatively hard material such as polycarbonate or polypropylene) includes a first end portion 74(1) and a second end portion 74(2). The first end portion 74(1) provides an interfacing structure 75 structured to interface or otherwise attach to the frame module 20. The second end portion 74(2) is provided to a swivel joint 80 adapted to be connected to an air delivery tube.

As illustrated, the first end portion 74(1) of the elbow 74 provides a relatively large diameter which allows the potential for cleaner/smoother lines thereby contributing to the overall mask aesthetic and reduced obtrusiveness. In addition, the relatively large diameter elbow offers the potential for the patient's nose to protrude into the elbow cavity thereby permitting the mask to be brought closer to the patient's face (i.e., reduced obtrusiveness).

In the illustrated embodiment, the swivel joint 80 is provided to a short tube 82 (e.g., extendable and retractable tube) that interconnects the elbow with the air delivery tube. In an embodiment, the swivel joint 80 may be integrally formed in one piece with the short tube 82.

1.3.2 Vent Arrangement

In the illustrated embodiment, the vent arrangement 76 is in the form of a vent insert that is adapted to be removably supported within an outlet opening in the elbow 74. In an embodiment, the vent arrangement 76 includes a base adapted to be supported within the outlet opening, one or more grill components or media (e.g., filter, membrane, or other porous material) provided to the base and structured to diffuse vent flow, and a cover to maintain the grill components/media within the base. Only the cover 77 of the vent arrangement 76 is visible in FIGS. 1-4.

Exemplary embodiments of such a vent arrangement are disclosed in U.S. Provisional Patent Application No. 60/957,766, filed Aug. 24, 2007, which is incorporated herein by reference in its entirety.

However, it should be appreciated that the vent arrangement may include other suitable arrangements, e.g., vent insert with one or more vent holes.

Also, the elbow may provide an alternative venting arrangement to the vent insert. For example, as indicated in dashed lines in FIG. 4, the first end portion 74(1) of the elbow 74 (e.g., along the interfacing structure 75) may include one or more vent holes 276 for gas washout. The one or more holes 276 may be provided to a soft part (e.g., silicone seal as described below) and/or a hard part (e.g., polycarbonate, polypropylene) of the elbow. The holes 276 may extend around the entire perimeter of the first end portion 74(1) or may extend along one or more portions of the first end portion 74(1). It is noted that providing vent holes along the entire perimeter of the elbow may help to disperse the vent flow in use. However, other suitable hole arrangements, hole numbers, and/or hole shapes along the first end portion 74(1) and/or other portions of the elbow are possible.

1.3.3 AAV

The elbow 74 includes a slot to receive the AAV 85, a port 79 that is selectively closed by a flap portion 86 of the AAV 85 (depending on the presence of pressurized gas), and structure for attaching the AAV 85, e.g., with a snap-fit.

The AAV 85 includes a flap portion 86 and a clip portion 88 provided to the flap portion 86 for attaching the AAV 85 to the elbow 74. In the illustrated embodiment, the flap portion 86 and the clip portion 88 are co-molded with one another to form a one-piece, integrated component. However, the flap portion 86 and clip portion 88 may be secured to one another in other suitable manners, e.g., mechanical interlock.

In an embodiment, the flap portion 86 may be constructed of a relatively soft elastomeric material (e.g., silicone) and the clip portion 88 may be constructed of a more rigid material (e.g., rigid plastic) for interfacing with the elbow 74.

The clip portion 88 of the AAV 85 includes structure for removably interlocking with the elbow 74, e.g., with a snap-fit. For example, the clip portion 88 may include tabs structured to interlock with respective recesses/protrusions provided to the elbow 74.

Alternative embodiments of the AAV are disclosed in PCT Application No. PCT/AU2006/000031, which is incorporated herein by reference in its entirety.

1.3.4 Elbow Module Attachment to Frame Module

The frame module 20 is structured to maintain the elbow module 70 in an operative position with respect to the patient's face. That is, the frame module 20 acts as a carrier and bearing surface for the elbow module 70. The frame module 20 and elbow module 70 may connect with a friction fit, snap-fit, mechanical interlock, or other suitable attachment mechanism. However, other suitable arrangements for attaching the elbow module to the frame module are possible.

In the illustrated embodiment, the elbow module 70 may be rotatably attached to the frame module 20 so that the elbow module 70 may be rotated relative to the frame module 20 in use, e.g., 360° rotation. This arrangement allows the elbow module 70 to assume different orientations in use, e.g., depending on patient preference. For example, the elbow module 70 may assume a first orientation so that the elbow extends generally downwardly from the mask to direct the air delivery tube under the patient's head in use. Alternatively, the elbow module 70 may be rotated and assume a second orientation so that the elbow extends upwardly from the mask to direct the air delivery tube over the patient's head in use. In an embodiment, the frame module 20 and elbow module 70 may be constructed of dissimilar materials to prevent or at least reduce squeak between the components in use.

1.4 Interface Seal

In an embodiment, a seal may be provided at the interface between the elbow module 70 and the frame module 20, at the interface between the cushion module 40 and the frame module 20, and/or at the interface between the elbow module 70 and the frame module 20. For example, a seal (e.g., elastomeric, ring-shaped seal) may be formed separately from the modules and attached at the interface (e.g., sandwiched between modules, adhesive, etc.). Alternatively, a seal may be co-molded with one or more of the modules. In an embodiment, a silicone lip seal may be provided to the cushion module to seal against the elbow module, thereby reducing leak.

In another embodiment, the interfacing structure 75 of the elbow module 70 may be constructed of a relatively soft, sealing material (e.g., silicone, which may be co-molded to the harder material of the elbow) that is structured to provide a seal at the interface between the elbow module 70 and the frame module 20. Also, the relatively soft interfacing structure 75 (e.g., silicone) provides a "soft" attachment to the relatively hard frame 20 (e.g., polycarbonate, polypropylene) which may allow an interference type fit. As noted above, one or more vent holes may be provided to the softer interfacing structure and/or the harder elbow.

1.5 Headgear

Headgear 90 may be removably attached to the headgear connectors 24, 25 of the frame module 20 to maintain the mask system in a desired position on the patient's face.

In the illustrated embodiment, the headgear 90 includes a pair of upper and lower straps 92, 94 with the upper straps 92 removably attached to respective upper headgear connectors 24 and the lower straps 94 removably attached to respective lower headgear connectors 25. The free end of each strap may include a Velcro® tab structured to engage the remainder of the strap to secure the strap in place. Such Velcro® attachment also allows adjustment of the length of the straps. However, the upper and lower headgear straps 92, 94 may be secured to the frame module 20 in any other suitable manners, e.g., adjustable ladder-lock arrangement, etc.

The headgear 90 also includes an upper strap 96 adapted to pass over the top of the patient's head in use and a rear strap 98 adapted to pass behind the patient's head in use.

The headgear 90 is structured to be self-supporting.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. Furthermore, each individual component of any given assembly, one or more portions of an individual component of any given assembly, and various combinations of components from one or more embodiments may include one or more ornamental design features. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A full face mask system for treatment of respiratory disorder with Continuous Positive Airway Pressure equipment suitable to generate a supply of gas at positive pressure to be delivered to a patient's airways, the mask system comprising:

a frame module;

a cushion module provided to the frame module and adapted to form a seal with the patient's nose and mouth;

an elbow module provided to the frame module and adapted to be connected to an air delivery tube to deliver breathable gas to the patient; and headgear removably attachable to the frame module, wherein:

the frame module is structured to assist in maintaining the cushion module and the elbow module in an operative position with respect to the patient's face, the frame module includes an open construction, said frame module being structured to retain the elbow module, the frame module includes two headgear connectors to connect with the headgear, the two headgear connectors each including a slot at a free end of the connector adapted to receive a respective headgear strap of the headgear, each said headgear connector is removably coupled to the frame module, each said headgear connector including a clip structure adapted to removably engage with a corresponding portion of the frame module, the cushion module is structured to interface with the frame module, the cushion module includes a main body of relatively harder material and a cushion of relatively softer material provided to the main body, the main body defining a breathing chamber and being adapted to interface with the frame module, the cushion provides a sealing portion adapted to form the seal with the patient's nose and mouth, wherein a portion of the main body is exposed and remains uncovered by the frame module when the frame module and the main body are engaged, the main body includes an entry opening for the introduction of the supply of gas into the breathing chamber, the opening being adapted to fluidly communicate with the elbow module, the cushion is a full-face cushion adapted to engage the patient's face generally along nasal bridge, cheek, and chin regions of the patient's face, the cushion includes a base wall provided to the main body, an undercushion layer extending away from the base wall, and a membrane provided to substantially cover the undercushion layer, the undercushion layer is provided in a nasal bridge region of the cushion, the undercushion layer is not provided in at least a part of a chin region of the cushion, the frame module is structured to hold the cushion module in an operative position with respect to the patient's face, the elbow module includes an elbow, a vent arrangement provided to the elbow for gas washout, and an anti-asphyxia valve provided to the elbow, the elbow includes a first end portion and a second end portion, the first end portion being attached to the frame module, the second end portion being provided to a swivel joint adapted to be connected to the air delivery tube, the vent arrangement comprises a vent insert that is adapted to be supported within an outlet opening in the elbow, the vent insert having one or more vent holes, the elbow includes a port that is selectively closed by a flap portion of the anti-asphyxia valve depending on the presence of pressurized gas, and a structure to attach the anti-asphyxia valve, the structure being positioned between the swivel joint and the vent arrangement, the frame module is structured to maintain the elbow module in an operative position with respect to the patient's face, and the elbow module is rotatably attached to the frame module so that the elbow module is permitted to be rotated 360 degrees relative to the frame module.

2. The mask system according to claim 1, wherein the frame module includes a forehead support.

3. The mask system according to claim 2, further comprising two additional headgear connectors.

4. The mask system according to claim 3, further comprising a concertina section that is provided in a nasal bridge region of the cushion, the concertina section including one or more folds that provide a degree of flexibility or movement relative to the main body without compromising the seal.

5. The mask system according to claim 4, wherein the concertina section is provided around the entire perimeter of the cushion.

6. The mask system according to claim 5, wherein flexibility of the concertina section is varied in different regions of the cushion.

7. The mask system according to claim 6, wherein the concertina section in the nasal bridge region has a relatively high degree of flexibility and the concertina section in a chin region of the cushion has a relatively low degree of flexibility.

8. The mask system according to claim 7, wherein the flexibility of the concertina section is varied by varying a wall length and a depth of the one or more folds.

9. The mask system according to claim 1, wherein the mask system is provided with a number of different sized cushion modules, the main body of each cushion module including a common configuration for interfacing with the frame module, thus providing a modular arrangement that allows the frame module to be selectively and removably coupled to each of the number of cushion modules and that allows the cushion modules to be selectively and removably coupled to each of a plurality of differently sized frame modules.

10. The mask system according to claim 9, wherein the different cushion modules include different size cushions, including small, medium, and large.

11. The mask system according to claim 10, wherein the main body and cushion are co-molded with one another to form an integrated co-molded component, the relatively harder material of the main body comprising first molded material adapted to interface with the frame module, and the relatively softer material of the cushion comprises a second molded material adapted to interface with patient's face.

12. The mask system according to claim 11, wherein the integrated co-molded component comprises a chemical bond between the first and second molded materials.

13. The mask system according to claim 12, wherein the integrated co-molded component does not include a mechanical interlock.

14. The mask system according to claim 1, further comprising a mechanical interlock to mechanically interlock the elbow module and the frame module to form a combined elbow and frame module, and a snap-fit attachment mechanism that releasably snap-fits the combined elbow and frame module with the main body of the cushion module.

15. A full face mask system for treatment of a respiratory disorder with Continuous Positive Airway Pressure (CPAP) or Non-Invasive Positive Pressure Ventilation (NIPPV) equipment suitable to generate a supply of gas at positive pressure to be delivered to a patient's airways, the mask system comprising:

a frame module;

a cushion module provided to the frame module and adapted to form a seal with the patient's nose and mouth;

an elbow module provided to the frame module and adapted to be connected to an air delivery tube to deliver breathable gas to the patient;

headgear removably attachable to the frame module, and four headgear connectors to connect with the headgear, two of the headgear connectors including an arm and a slot at a free end of the arm adapted to receive a respective headgear strap of the headgear, each arm being at least semi-rigid to stabilize the mask system on the patient's face, each arm is removably coupled to the frame module, each said arm including clip structure adapted to removably engage with a corresponding portion of the frame module, wherein:

the frame module is structured to maintain the cushion module and the elbow module in an operative position with respect to the patient's face, the frame module includes an engaging portion structured to engage the cushion module, the cushion module is structured to interface with the frame module, the cushion module includes a main body of polycarbonate material and a cushion of silicone material provided to the main body, the main body defining a breathing chamber and being adapted to interface with the frame module, wherein a portion of an exterior surface of the main body remains exposed when the main body and the frame module are engaged, the cushion provides a sealing portion adapted to form the seal with the patient's nose and mouth, the main body includes an entry opening for the introduction of the supply of gas into the breathing chamber, the opening being adapted to communicate with the elbow module, the cushion is a full-face cushion adapted to engage the patient's face generally along nasal bridge, cheek, and chin regions of the patient's face, the cushion includes a base wall provided to the main body, an undercushion layer extending away from the base wall, and a membrane provided to substantially cover the undercushion layer, the undercushion layer is provided in a nasal bridge region of the cushion, the undercushion layer is not provided in at least a part of a chin region of the cushion, the frame module is shaped and structured to hold the cushion module in an operative position with respect to the patient's face, the frame module including an interfacing structure along an inner edge that is adapted to interface with a portion of the main body of the cushion module, the elbow module includes an elbow, a vent arrangement provided to the elbow for gas washout, and an anti-asphyxia valve provided to the elbow, the elbow includes a first end portion and a second end portion, the first end portion being attached to the frame module, the second end portion having a swivel joint adapted to be connected to the air delivery tube, the vent arrangement comprises a vent insert that is adapted to be supported within an outlet opening in the elbow, the vent insert having one or more vent holes, the elbow includes a port that is selectively closed by a flap portion of the anti-asphyxia valve depending on the presence of pressurized gas, and a structure to attach the anti-asphyxia valve, the structure being positioned between the swivel joint and the vent arrangement, the frame module is structured to maintain the elbow module in an operative position with respect to the patient's face, the elbow module is rotatably attached to the frame module so that the elbow module is rotatable 360 degrees relative to the frame module and the cushion module, the headgear is removably attachable to the headgear connectors to maintain the mask system in a desired position on the patient's face, the headgear includes a pair of upper and lower straps and a rear strap adapted to pass behind the patient's head, the upper straps being removably attached to respective upper headgear connectors and the lower straps being removably attached to respective lower headgear connectors, a free end of each strap including a hook and loop tab structured to adjustably engage the remainder of the strap to secure the strap in place.

16. The mask system according to claim 15, wherein the frame module includes a forehead support.

17. The mask system according to claim 16, further comprising a concertina section provided in the nasal bridge region of the cushion of the cushion module, the concertina section including one or more folds that provide a degree of flexibility or movement.

18. The mask system according to claim 17, wherein the concertina section is provided around the entire perimeter of the cushion of the cushion module.

19. The mask system according to claim 18, wherein flexibility of the concertina section is varied in different regions of the cushion of the cushion module.

20. The mask system according to claim 19, wherein the concertina section in the nasal bridge region has a different degree of flexibility compared to the concertina section in the chin region.

21. The mask system according to claim 20, wherein the flexibility of the concertina section is varied by varying a wall length and/or a depth of the one or more folds.

22. The mask system according to claim 15, wherein the main body includes a universal configuration adapted to interface with the frame module, the main body being adapted to connect with a plurality of cushions of different sizes, thus providing a modular arrangement that allows the frame module to be selectively and removably coupled to each of a plurality of differently sized cushion modules.

23. The mask system according to claim 22, wherein the differently sized cushion modules include different size cushions, including small, medium, and large.

24. The mask system according to claim 23, wherein the main body and cushion are co-molded with one another to form an integrated co-molded component, the polycarbonate material of the main body comprising a first molded material adapted to interface with the frame module, and the silicone material of the cushion comprises a second molded material adapted to interface with patient's face.

25. The mask system according to claim 24, wherein said integrated co-molded component comprises a chemical bond.

26. The mask system according to claim 25, wherein the integrated co-molded component does not include a mechanical interlock.

27. The mask system according to claim 15, wherein the elbow module and the frame module are mechanically interlocked via a mechanical interlock to form a combined elbow and frame module, the combined elbow and frame module including a snap-fit attachment mechanism that releasable snap-fits with the main body of the cushion module.

28. An oro-nasal mask system for treatment of respiratory disorder with Continuous Positive Airway Pressure equipment suitable to generate a supply of gas at positive pressure to be delivered to a patient's airways, the mask system comprising:

a frame module;

a cushion module having (i) a cushion adapted to form a seal with the patient's nose and mouth and (ii) a main hub body;

an elbow module adapted to be connected to an air delivery tube to deliver breathable gas to the patient; and headgear removably attachable to the frame module, wherein:

the frame module includes two headgear connectors to connect with the headgear, each of the two headgear connectors including a slot at a free end of the connector adapted to receive a respective headgear strap of the headgear, each said headgear connector is removably coupled to the frame module, each said headgear connector including a clip structure adapted to removably engage with a corresponding portion of the frame module, the main hub body comprises a relatively harder material and the cushion comprises relatively softer material provided to the main hub body, the cushion is an oro-nasal cushion adapted to engage the patient's face generally along nasal bridge, cheek, and chin regions of the patient's face, the cushion includes a base wall provided to the main hub body, an undercushion layer extending away from the base wall, and a membrane provided to substantially cover the undercushion layer, the undercushion layer is provided in a nasal bridge region of the cushion, the elbow module includes an elbow, a vent arrangement provided to the elbow for gas washout, and an anti-asphyxia valve provided to the elbow, the elbow includes a first end portion and a second end portion, the first end portion being attached to the frame module, the second end portion being provided to a swivel joint adapted to be connected to the air delivery tube, the vent arrangement comprises a vent insert that is adapted to be supported within an outlet opening in the elbow, the vent insert having one or more vent holes, the elbow includes a port that is selectively closed by a flap portion of the anti-asphyxia valve depending on the presence of pressurized gas, and a structure to attach the anti-asphyxia valve, the structure being positioned between the swivel joint and the vent arrangement, the elbow module is rotatably attached to the frame module with a mechanical interlock so that the elbow module is permitted to be rotated 360 degrees relative to the frame module, the elbow module and the frame module comprise a combined elbow and frame module that is releasably snap-fitted to the cushion module with a snap-fit attachment mechanism.

29. An oro-nasal mask system for treatment of a respiratory disorder with Continuous Positive Airway Pressure (CPAP) or Non-Invasive Positive Pressure Ventilation (NIPPV) equipment suitable to generate a supply of gas at positive pressure to be delivered to a patient's airways, the mask system comprising:

a frame module;

a cushion module engaged with the frame module;

an elbow module rotatably attached to the frame module with a mechanical interlock and adapted to be connected to an air delivery tube to deliver breathable gas to the patient;

headgear removably attachable to the frame module, and four headgear connectors to connect with the headgear, two of the headgear connectors including an arm and a slot at a free end of the arm adapted to receive a respective headgear strap of the headgear, each arm being at least semi-rigid to stabilize the mask system on the patient's face, each arm is removably coupled to the frame module, each said arm including clip structure adapted to removably engage with a corresponding portion of the frame module, wherein:

the cushion module includes a main hub body and a cushion provided to the main hub body, the cushion is an oro-nasal cushion adapted to seal generally along nasal bridge, cheek, and chin regions of the patient's face, the elbow module includes an elbow, a vent arrangement provided to the elbow for gas washout, and an anti-asphyxia valve provided to the elbow, the elbow includes a first end portion and a second end portion, the first end portion being attached to the frame module with the mechanical interlock, the second end portion having a swivel joint adapted to be connected to the air delivery tube, the vent arrangement comprises a vent insert that is adapted to be supported within an outlet opening in the elbow, the vent insert having one or more vent holes, the elbow includes a port that is selectively closed by a flap portion of the anti-asphyxia valve depending on the presence of pressurized gas, and a structure to attach the anti-asphyxia valve, the structure being positioned between the swivel joint and the vent arrangement, the elbow module is rotatably attached to the frame module so that the elbow module is rotatable 360 degrees relative to the frame module and the cushion module, the headgear is removably attachable to the headgear connectors to maintain the mask system in a desired position on the patient's face, the headgear includes a pair of upper and lower straps and a rear strap adapted to pass behind the patient's head, the upper straps being removably attached to respective upper headgear connectors and the lower straps being removably attached to respective lower headgear connectors, a free end of each strap including a hook and loop tab structured to adjustably engage the remainder of the strap to secure the strap in place, the elbow module and the frame module comprise a combined elbow and frame module due to being mechanically interconnected by the mechanical interlock, and a snap-fit attachment mechanism releasably snap-fits the combined elbow and frame module with the cushion module.

30. The mask system according to claim 29, wherein the mechanical interlock is separate from the snap-fit attachment mechanism.

* * * * *